US012742023B2

(12) United States Patent
Inubushi et al.

(10) Patent No.: US 12,742,023 B2
(45) Date of Patent: Sep. 22, 2026

(54) VINYL ACETATE, VINYL ACETATE POLYMER, AND VINYL ALCOHOL POLYMER

(71) Applicant: KURARAY CO., LTD., Okayama (JP)

(72) Inventors: Yasutaka Inubushi, Tokyo (JP); Keishi Hachiya, Okayama (JP); Masaki Kato, Okayama (JP); Yoshikazu Yamasaki, Okayama (JP); Makoto Okamoto, Pasadena, TX (US); Kazuyuki Somemiya, Niigata (JP); Takafumi Izawa, Okayama (JP)

(73) Assignee: KURARAY CO., LTD., Okayama (JP)

( * ) Notice: Subject to any disclaimer, the term of this patent is extended or adjusted under 35 U.S.C. 154(b) by 616 days.

(21) Appl. No.: 18/003,775

(22) PCT Filed: Jun. 30, 2021

(86) PCT No.: PCT/JP2021/024729

§ 371 (c)(1),
(2) Date: Dec. 29, 2022

(87) PCT Pub. No.: WO2022/004782

PCT Pub. Date: Jan. 6, 2022

(65) Prior Publication Data

US 2023/0257491 A1 Aug. 17, 2023

(30) Foreign Application Priority Data

Jun. 30, 2020 (JP) ................................ 2020-112959
Apr. 28, 2021 (JP) ................................ 2021-075727

(51) Int. Cl.
*C07C 69/15* (2006.01)
*C08F 8/12* (2006.01)
*C08F 16/06* (2006.01)
*C08F 18/08* (2006.01)

(52) U.S. Cl.
CPC .............. *C08F 16/06* (2013.01); *C07C 69/15* (2013.01); *C08F 8/12* (2013.01); *C08F 18/08* (2013.01)

(58) Field of Classification Search
CPC .......... C08F 16/06; C08F 216/06; C08F 8/12; C08F 18/08; C08F 118/08; C07C 69/15
See application file for complete search history.

(56) References Cited

U.S. PATENT DOCUMENTS 4,021,476 A * 5/1977 Harbuck ................. C07C 67/54 560/241
4,407,991 A * 10/1983 Messick ................. C08K 5/092 524/321
2002/0068806 A1* 6/2002 Yoshimi ..................... C08J 5/18 526/330
2006/0258803 A1 11/2006 Stark
2011/0160419 A1* 6/2011 Dubois .................. C07C 45/52 526/330
2011/0287204 A1† 11/2011 Devisme
2013/0043384 A1* 2/2013 Matsumoto ........... C08F 220/06 250/282
2013/0143973 A1† 6/2013 Townsend
2014/0213701 A1 7/2014 Nonaka et al.
2015/0291761 A1 10/2015 Iacobucci et al.
2017/0158791 A1* 6/2017 Matsumoto ............ B01J 20/261
2017/0166670 A1 6/2017 Matsumoto et al.
2017/0183430 A1* 6/2017 Devisme ............ C09J 123/0853

FOREIGN PATENT DOCUMENTS

CN 1350010 A 5/2002
CN 1832983 A 9/2006
CN 102858816 A 1/2013
CN 109879996 A † 6/2019
EP 2565212 A1 3/2013
EP 3438138 A1 2/2019
FR 2934264 A1 * 1/2010 .......... C07C 51/377
JP 2000-159825 * 6/2000
JP 2001-253993 A 9/2001
JP WO2011/132592 A1 10/2011
JP WO2011/136237 A1 11/2011
JP WO2011/136238 A1 11/2011
JP 2016-145263 A 8/2016
JP 2017127975 A 7/2017
JP 2017-219428 † 12/2017
JP 2017-219428 A 12/2017
JP 2019-151341 A 9/2019
JP WO2020/004608 A1 1/2020
(Continued)

OTHER PUBLICATIONS

Livshits, Izvestiya Akademii Kauk SSSR, Seriya Khimicheskaya, No. 10, pp. 1860-1861, Oct. 1966 (Year: 1966).*
Translation of JP 2000-159825 (Year: 2000).*
Translation of FR 2934264 (Year: 2010).*
Office Action issued in the corresponding Chinese Application No. 2021800460978, date Feb. 26, 2024.
Decision on Rejection issued on the corresponding JP Aplication No. 2022-534077, dated Jul. 1, 2025.
Decision on Rejection issued in corresponding Chinese Patent Application No. 202180046097.8, dated Mar. 22, 2025.
Office Action issued in corresponding Japanese Patent Application No. 2022-534077, dated Feb. 18, 2025.
(Continued)

*Primary Examiner* — Robert C Boyle
(74) *Attorney, Agent, or Firm* — Morgan, Lewis & Bockius LLP

(57) ABSTRACT

[Problem to be solved] To provide a traceable vinyl acetate, a polymer containing the vinyl acetate, and a vinyl alcohol polymer which is a saponified product of the polymer.

[Solution] Vinyl acetate having a ratio of carbon-14 to total carbon of $1.0\times10^{-14}$ or more, a vinyl acetate polymer containing the vinyl acetate as a monomer unit and a vinyl alcohol polymer obtained by saponifying the vinyl acetate polymer.

31 Claims, 1 Drawing Sheet

(56) References Cited

FOREIGN PATENT DOCUMENTS

| | | | |
|---|---|---|---|
| TW | 201428038 A | | 7/2014 |
| WO | 2012-063954 | † | 5/2012 |
| WO | 2012/063954 A1 | | 5/2012 |
| WO | 2019/202405 A1 | | 10/2019 |

OTHER PUBLICATIONS

Office Action issued for the corresponding Chinese Application No. 2021800460978 on Nov. 22, 2024.

Office Action issued for the corresponding Taiwan Application No. 110123979 on Nov. 20, 2024.

Search Report issued for the corresponding Singapore Application No. 11202261623T on Oct. 3, 2024.

Jones et al., "The Production of Vinyl Acetate Monomer as a Co-Product from the Non-Catalytic Cracking of Soybean Oil," Processes, 3: 619-633 (2015).

WACKER Presents the First Ever Renewables-Based Dispersible Polymer Powder for Construction Applications via the Mass Balance Approach, Mar. 24, 2020.

Planavsky et al., "Carbon Isotopes as a Geochemical Tracer," Encyclopedia of Astrobiology, 241-245 (2011) (abstract only).

Third Party Observations filed in corresponding International Patent Application No. PCT/JP2021/024729 dated Oct. 27, 2022.

International Search Report issued in corresponding International Patent Application No. PCT/JP2021/024729 dated Aug. 3, 2021.

Saito, "Multipurpose Use of Sugar: Use for intermediate chemical raw materials obtained by fermentation," submitted with third party observations dated Oct. 27, 2022 (see partial English translation).

Office Action issued in corresponding Taiwanese Patent Application No. 114132414, dated Jan. 5, 2026.

* cited by examiner
† cited by third party

VINYL ACETATE, VINYL ACETATE POLYMER, AND VINYL ALCOHOL POLYMER

TECHNICAL FIELD

The present invention relates to traceable vinyl acetate, a polymer containing the vinyl acetate as a monomer unit, and a saponified product of the polymer.

RELATED ART

Vinyl acetate is used as a raw material for vinyl acetate resins and vinyl alcohol resins, and also as a monomer for copolymerization with ethylene, styrene, acrylate, methacrylate, and the like. The resulting resins and copolymers are important industrial materials that are used in a wide range of fields such as paints, adhesives and fiber processing agents.

Among them, vinyl alcohol polymers (hereinafter, may be referred to as "PVOH") obtained by polymerizing vinyl acetate and saponifying the resulting polymer are one kind of the few crystalline water-soluble polymers and are widely used as emulsifiers, suspending agents, surfactants, various binders, adhesives, fiber processing agents, paper processing agents, films, fibers, fabrics and the like by utilizing its excellent water solubility and film properties (strength, oil resistance, film-forming properties, oxygen gas barrier properties, etc.).

Further, ethylene-vinyl alcohol copolymers (hereinafter, may be referred to as "EVOH") obtained by copolymerizing vinyl acetate and ethylene and saponifying the resulting copolymer are excellent in transparency, gas barrier properties against various gases such as oxygen, fragrance retention, solvent resistance, oil resistance, anti-static property, mechanical strength, or the like, and taking advantage of these characteristics, are widely used in various packaging containers such as food packaging containers, pharmaceutical packaging containers, industrial chemical packaging containers, agricultural chemical packaging containers, and the like. When producing such a molded product, secondary processing is often performed after an ethylene-vinyl alcohol copolymer is melt-molded. For example, stretching for the purpose of improving mechanical strength and thermoforming of a multilayer sheet containing an ethylene-vinyl alcohol copolymer layer to form a container shape are widely practiced.

As such, the vinyl alcohol polymers and the ethylene-vinyl alcohol copolymers are used in a wide range of applications, and it is responsibility of suppliers to supply high-quality products to markets. Further, there is a need for a method of distinguishing one's own products from products of other companies for branding purposes.

For example, the ethylene-vinyl alcohol copolymers used in gas barrier layers of commercially available packaging containers are formed into packaging containers by thermoforming, but the ethylene-vinyl alcohol copolymers may form a solvent-insoluble gel due to heat history received during thermoforming. Therefore, even if the packaging container is recovered and the ethylene-vinyl alcohol copolymer used therein is extracted with a solvent to measure a molecular weight of the ethylene-vinyl alcohol copolymer, it is often difficult to measure the molecular weight accurately. Therefore, it is not possible to determine whether or not the ethylene-vinyl alcohol copolymer is the in-house ethylene-vinyl alcohol copolymer only by analyzing the molded article.

Therefore, when vinyl acetate produced, polymers and copolymers obtained therefrom, and saponified products of the polymers and the copolymers are used in paints, adhesives, textile processing agents, paper processing agents, films, fibers, fabrics, food packaging containers, pharmaceutical packaging containers, industrial chemical packaging containers, agricultural chemical packaging containers, and the like through many distribution channels and then are discarded, It is difficult to determine from which factory and from which production line the resin and the packaging container after its use have been manufactured.

As one of methods for tracing the in-house products, for example, a method of adding a tracer substance to a vinyl alcohol polymer is conceivable. However, the addition of tracers sometimes causes cost increase and performance deterioration of the vinyl alcohol polymer.

SUMMARY OF THE INVENTION

Problem to be Solved by the Invention

The present inventors focused on carbon isotopes contained in vinyl acetate and have found that by using vinyl acetate containing a certain amount of a specific carbon isotope, it is possible to trace resulting polymer and copolymer and to determine whether a raw material is the in-house product even if a final product is discarded.

That is, an object of the present invention is to provide traceable vinyl acetate, a polymer containing the vinyl acetate as a monomer unit and a vinyl alcohol polymer which is a saponified product of the polymer.

Means for Solving the Problem

The present invention provides vinyl acetate shown below, a polymer containing the vinyl acetate as a monomer unit, and a saponified product of the polymer.

[1] Vinyl acetate having a ratio of carbon-14 to total carbon of $1.0\times10^{-14}$ or more.

[2] The vinyl acetate in the above-mentioned item [1], having a carbon stable isotope ratio of −20‰ or more.

[3] The vinyl acetate in the above-mentioned item [1], having a carbon stable isotope ratio of less than −20‰.

[4] The vinyl acetate in any one of the above-mentioned items [1] to [3], containing a sulfur component in an amount of more than 0 ppm and 100 ppm or less.

[5] The vinyl acetate in the above-mentioned item [4], wherein the sulfur component is dimethylsulfide or dimethylsulfoxide.

[6] The vinyl acetate in any one of the above-mentioned items [1] to [5], containing an acetate ester in an amount of 10 ppm to 1,500 ppm.

[7] The vinyl acetate in the above-mentioned item [6], wherein the acetate ester is at least one of methyl acetate and ethyl acetate.

[8] The vinyl acetate in any one of the above-mentioned items [1] to [7], containing a polymerization inhibitor in an amount of more than 0 ppm and 100 ppm or less.

[9] The vinyl acetate in any one of the above-mentioned items [1] to [8], containing at least one compound selected from a polyvalent carboxylic acid, a hydroxycarboxylic acid and a hydroxylactone-based compound in an amount of 1 ppm to 500 ppm.

[10] The vinyl acetate in any one of the above-mentioned items [1] to [9], containing acetaldehyde dimethylacetal in an amount of 0.001 to 10 parts by mass.

[11] A vinyl acetate polymer containing the vinyl acetate in any one of the above-mentioned items [1] to [10] as a monomer unit.

[12] A vinyl alcohol polymer obtained by saponifying the vinyl acetate polymer in the above-mentioned item [11].

[13] The vinyl alcohol polymer in the above-mentioned item [12], further containing ethylene units in a content of 1 mol% or more and 60mol% or less.

[14] The vinyl alcohol polymer in the above-mentioned item [12] or [13], having a degree of saponification of 80 mol% or more.

[15] The vinyl alcohol polymer in any one of the above-mentioned items [12] to [14], having a viscosity-average polymerization degree of 200 or more and 5,000 or less.

[16] The vinyl alcohol polymer in any one of the above-mentioned items [12] to [15], wherein a content of 1, 2-glycol bond is in the range of 0.2 mol% or more and 2 mol% or less.

[17] The vinyl alcohol polymer in any one of the above-mentioned items [12] to [16], wherein a ratio of carbon-14 to total carbon is $1.0\times10^{-14}$ or more.

[18] The vinyl alcohol polymer in any one of the above-mentioned items [12] to [17], having a carbon stable isotope ratio of −20‰ or more.

[19] The vinyl alcohol polymer in any one of the above-mentioned items [12] to [17], having a carbon stable isotope ratio of less than −20‰.

[20] The vinyl alcohol polymer in any one of the above-mentioned items [12] to [19], containing a sulfur component in an amount of more than 0 ppm and 100 ppm or less.

[21] The vinyl alcohol polymer in the above-mentioned item [20], wherein the sulfur component is dimethylsulfide or dimethylsulfoxide.

[22] The vinyl alcohol polymer in any one of the above-mentioned items [12] to [21], wherein a content of ethylene units is in the range of 1 mol% or more and 15 mol% or less, and a degree of saponification is in the range of 85 mol% or more and 99.9 mol% or less, and wherein the vinyl alcohol polymer has a propyl group at a terminal end thereof and a content of the propyl group with respect to total monomer units is in the range of 0.0005 mol% or more and 0.1 mol% or less.

[23] The vinyl alcohol polymer in any one of the above-mentioned items [12] to [22], wherein the vinyl alcohol polymer has an alkoxy group at a terminal end thereof and a content of the alkoxy group with respect to total monomer units is in the range of 0.0005 mol% or more and 1 mol% or less.

[24] The vinyl alcohol polymer in any one of the above-mentioned items [12] to [23], wherein the vinyl alcohol polymer has a following structure (I) and structure (II) at a terminal end thereof and a total content of the structure (I) and the structure (II) with respect to total monomer units constituting the vinyl alcohol polymer is in the range of 0.001 mol% or more and 0.1 mol% or less.

[Formula 1]

(I)

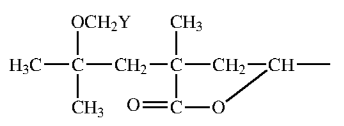

where Y is a hydrogen atom or a methyl group.

[Formula 2]

(II)

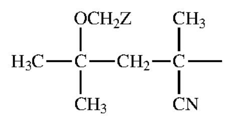

where Z is a hydrogen atom or a methyl group.

[25] The vinyl alcohol polymer in the above-mentioned item [24], wherein a content of ethylene units is in the range of 1 mol% or more and 15 mol% or less, and a degree of saponification is in the range of 85 mol% or more and 99.9 mol% or less, and wherein a molar ratio R [I/(I+II)] of the structure (I) to a total of the structure (I) and the structure (II) satisfies a following formula (1).

$$R < 0.92 - Et/100 \quad (1)$$

where Et is the content of the ethylene units (mol%).

[26] The vinyl alcohol polymer in any one of the above-mentioned items [13], [22] and [25], wherein a block character of ethylene units is in the range of 0.90 to 0.99.

[27] The vinyl alcohol polymer in the above-mentioned item [24] or [25], wherein a content of ethylene units is in the range of 15 mol% or more and 60 mol% or less, and a degree of saponification is in the range of 85 mol% or more and 99.9 mol% or less, and wherein a total content of the structure (I) and the structure (II) with respect to total monomer units constituting the vinyl alcohol polymer is in the range of 0.002 mol% or more and 0.02 mol% or less, and a molar ratio R [I/(I+II)] of the structure (I) to a total of the structure (I) and the structure (II) satisfies a following formula (2) expressed using the content of the ethylene units Et in the vinyl alcohol polymer.

$$0.8 < R + Et/100 \quad (2)$$

[28] A method for tracing a polymer using vinyl acetate having a ratio of carbon-14 to total carbon of $1.0\times10^{-14}$ or more.

[29] The method for tracing a polymer using vinyl acetate in the above-mentioned item [28], wherein a carbon stable isotope ratio of the vinyl acetate is −20‰ or more.

[30] The method for tracing a polymer using vinyl acetate in the above-mentioned item [28], wherein a carbon stable isotope ratio of the vinyl acetate is less than −20‰.

[31] A method for tracing a polymer using a vinyl acetate polymer containing the vinyl acetate in any one of the above-mentioned items [28] to [30] as a monomer unit.

[32] A method for tracing a polymer using a vinyl alcohol polymer obtained by saponifying the vinyl acetate polymer in the above-mentioned item [31].

Effects of the Invention

According to the present invention, it is possible to provide traceable vinyl acetate, a polymer containing the vinyl acetate and a vinyl alcohol polymer which is a saponified product of the polymer.

MODE FOR CARRYING OUT THE INVENTION

Figure 1:
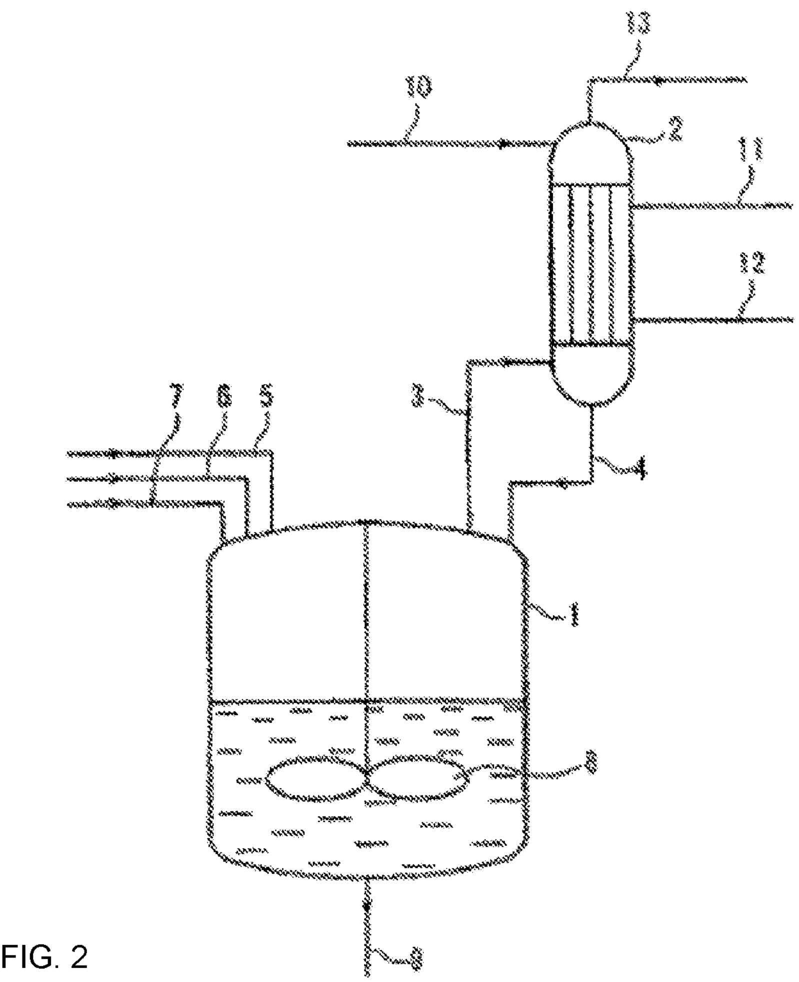
FIG. 1 is a schematic diagram of a polymerization apparatus used in Example 46.

Hereinafter, vinyl acetate according to the present invention, a vinyl acetate polymer obtained by polymerizing the vinyl acetate, and the vinyl alcohol polymer which is a saponified product of the vinyl acetate polymer will be described in detail.

Vinyl acetate obtained from conventional petroleum feedstocks has a ratio of carbon-14 (hereinafter, may be referred to "$^{14}C$") to total carbon (hereinafter, may be referred to "$^{14}C/C$") of less than $1.0\times10^{-14}$, whereas the vinyl acetate of the present invention has $^{14}C/C$ of $1.0\times10^{-14}$ or more. The total carbon means carbon including all isotopes of carbon.

From the viewpoint of ease of tracing, $^{14}C/C$ is preferably $1.0\times10^{-13}$ or more, more preferably $5.0\times10^{-13}$ or more. When almost 100% by mass is non-fossil raw material, an upper limit of $^{14}C/C$ is $1.2\times10^{-12}$, but appropriately, for example, $^{14}C/C$ of blank natural products such as oxalic acid standards are actually measured and the measured value may be set as the upper limit.

As a method for controlling the range of $^{14}C/C$ as described above, a method using the vinyl acetate derived from a natural product can be considered as described later. Artificial carbon-14 exists in nature, and a concentration of carbon-14 in natural products fluctuates over time. Therefore, when the vinyl acetate derived from the natural products is used, $^{14}C/C$ in the vinyl acetate can be determined by appropriately correcting the concentration of carbon-14 in the natural products. Further, a half-life of carbon-14 is 5,730 years, but decrease in an amount of carbon-14 is negligible considering the time from manufacture to market of typical chemical products.

Carbon-13 (hereinafter, may be referred to "$^{13}C$") and carbon-14 can be quantified by burning the vinyl acetate of interest into carbon dioxide and then analyzing the carbon dioxide or graphite, which is a reduced form thereof, by accelerator mass spectrometry (AMS method; Accelerator Mass Spectrometry). For example, for graphite ionized by Cs beam irradiation, the amounts of carbon-12 ions, carbon-13 ions, and carbon-14 ions are measured.

$^{14}C/C$ can be obtained by, for example, comparatively measuring a content of carbon-14 in oxalic acid, which is a standard substance created by the National Institute of Standards and Technology, by the accelerator mass spectrometry after conversion to the carbon dioxide or the graphite as described above.

The vinyl acetate as described above can be synthesized, for example, as follows. The vinyl acetate can usually be obtained by a gas phase reaction of ethylene, acetic acid and oxygen in a presence of a catalyst. At this time, by using the ethylene or the acetic acid containing a predetermined amount of carbon-14 in either or both of the ethylene and the acetic acid, the vinyl acetate containing the predetermined amount of carbon-14 can be obtained. The ethylene and the acetic acid containing the predetermined amount of carbon-14 include, for example, ethylene or acetic acid derived from biomass.

A term "biomass" refers to industrial resources originating from living organisms that are not exhaustible resources, and refers to renewable organic resources derived from organisms, excluding fossil resources.

The biomass takes in carbon dioxide from atmosphere through photosynthesis during its growth process. Therefore, burning the biomass and releasing the carbon dioxide does not increase an amount of the carbon dioxide in the atmosphere as a whole. This property is called carbon neutral, and it is preferable to use the ethylene and/or the acetic acid derived from the biomass from the viewpoint of global environment.

The biomass may be of a single origin or a mixture, and examples of the biomass include cellulosic crops such as pulp, kenaf, wheat straw, rice straw, waste paper and papermaking residue, fats such as rapeseed oil, cottonseed oil, soybean oil, coconut oil and castor oil, carbohydrate crops such as corn, potatoes, wheat, rice, chaff, rice bran, old rice, cassava and sago palm, essential oils such as pine oil, orange oil and *eucalyptus* oil, wood, charcoal, compost, natural rubber, cotton, sugarcane, bean curd refuse, bagasse, buckwheat, soybeans, pulp black liquor, vegetable oil cake, and the like. Further, the biomass is not limited to biofuel harvests, but includes agricultural residues, municipal waste, industrial waste, paper industry sludge, pasture waste, wood and forest waste, and the like.

The biomass-derived carbon refers to carbon present in the vinyl acetate synthesized from carbon that was present in the atmosphere as carbon dioxide and was taken up by plants. Since the atmosphere contains a certain amount of carbon-14, the certain amount of carbon-14 is contained in the ethylene and the acetic acid derived from the biomass that have taken in the carbon dioxide in the atmosphere. Normally, the ethylene and the acetic acid derived from the biomass contain carbon-14 in a ratio of $1.0\times10^{-12}$ or more to the total carbon.

On the other hand, fossil resources such as petroleum contain little carbon-14, and ethylene and acetic acid derived from fossil resources have the ratio of carbon-14 to total carbon of less than $1.0\times10^{-14}$. Therefore, by using the ethylene and the acetic acid derived from the biomass together with the ethylene and the acetic acid derived from the fossil raw material as vinyl acetate raw materials, $^{14}C/C$ of the obtained vinyl acetate can be adjusted to a desired value. For example, the vinyl acetate obtained from the biomass-derived ethylene and the biomass-derived acetic acid and the vinyl acetate obtained from the fossil resource-derived ethylene and the fossil resource-derived acetic acid may be mixed so that $^{14}C/C$ is a desired value, and the vinyl acetate may be obtained by using the ethylene and/or the acetic acid derived from the biomass and the ethylene and/or the acetic acid derived from the fossil resource in a desired ratio.

In addition, while a molecular weight of the ethylene derived from carbon-12 (hereinafter, may be referred to as "$^{12}C$") is 28.05, and a molecular weight of the acetic acid is 60.05, the ethylene and the acetic acid containing a large amount of carbon-13 and carbon-14 have large molecular weights. Therefore, Boiling points of the ethylene and the acetic acid are generally −103.7 °C and 117.9 °C, respectively, but the boiling points of the ethylene and the acetic acid each containing the large amount of carbon-13 and carbon-14 are slightly higher. The amounts of carbon-13 and carbon-14 can be adjusted by utilizing a boiling point difference derived from this molecular weight ratio, that is, that the smaller the molecular weight, the lower the boiling point. Specifically, carbon-13 and carbon-14 can also be made into a desired content by distillation purification of ethanol, which is the raw material of ethylene and acetic acid, ethylene obtained by dehydration reaction of ethanol, and acetic acid obtained by oxidation reaction of ethanol and vaporization during gas-phase dehydration and gas-phase oxidation of ethanol.

By setting the ratio of carbon-14 contained in the vinyl acetate within the above range, the vinyl acetate can be distinguished from ordinary vinyl acetate obtained from petroleum-derived ethylene. In addition, by appropriately changing $^{14}C/C$ for each product, each lot, or the like, it is possible to determine what kind of product the waste was used for, even from the collected waste. Therefore, the vinyl acetate of the present invention can be traced after production.

In addition to setting the ratio of carbon-14 in the vinyl acetate to the above range, it is preferable to set the carbon stable isotope ratio (hereinafter, may be referred to as "$\delta^{13}C$") to a specific range from the viewpoint of improving tracing accuracy.

The carbon stable isotope ratio means a ratio of carbon-13 to carbon-12 among three types of carbon atom isotopes, carbon-12, carbon-13, and carbon-14, which exist in nature. The carbon stable isotope ratio is expressed as a deviation from a standard substance and is a value (5 value) defined by the following formula (3).

[Equation 1]

$$\delta^{13}C[\%] = \{(^{13}C/^{12}C)_{sample}/(^{13}C/^{12}C)_{PDB} - 1.0\} \times 1{,}000 \quad (3)$$

In the formula, $[(^{13}C/^{12}C)_{sample}]$ represents a stable isotope ratio of an object to be measured, and $[(^{13}C/^{12}C)_{PDB}]$ represents a stable isotope ratio of the standard substance. The suffix PDB is an abbreviation for "Pee Dee Belemnite", which means a fossil of a pilaster made of calcium carbonate (as a standard substance, a fossil of a pilaster excavated from the Pee Dee Formation in South Carolina) and is used as the standard for the $^{13}C/^{12}C$ ratio. Further, the "carbon stable isotope ratio ($\delta^{13}C$)" is measured by accelerator mass spectrometry. Since standard substances are scarce, working standards with known stable isotope ratios can also be used.

By using the vinyl acetate with $\delta^{13}C$ of −20‰ or more, or the vinyl acetate with $\delta^{13}C$ of less than −20‰, tracing accuracy can be further improved. As a method for adjusting $\delta^{13}C$ to the above range, it is convenient to use the ethylene or the acetic acid derived from the biomass described above.

When the ethylene or the acetic acid derived from the biomass are used, as described later, the biomass is broadly classified into those derived from C3 plant such as sweet potato, sugar beet, rice, trees and algae, and those derived from C4 plant such as corn, sugarcane, and cassava, and the $\delta^{13}Cs$ of the two are different.

Plants are classified into three types, C3 plant, C4 plant, and succulent-type photosynthetic (CAM/Crassulacean Acid Metabolism) plant (hereinafter, may be referred to as "CAM plant"), depending on the type of initial carbon dioxide fixation product in the photosynthetic carbon dioxide fixation pathway.

More than 90% f the plants on earth belong to C3 plant, including agriculturally useful plants such as rice, wheat, tobacco, wheat, potato, and palm. An enzyme involved in the carbon dioxide fixation in the photosynthetic pathway of C3 plant is ribulose-1,5-bisphosphate carboxylase and have low affinity for the carbon dioxide and conversely high affinity for oxygen, resulting in low efficiency of the carbon dioxide fixation reaction and thus the photosynthetic reaction. Plants having only such a Calvin-Benson cycle are called C3 plant.

When $\delta^{13}C$ is less than −20‰, these C3 plant and mixtures thereof are widely applied as carbon sources, but rice, wheat, potato and palm oil are preferred as the carbon sources in terms of production volume and cost.

When using the biomass derived from C3 plant, from the viewpoint of improving the tracing accuracy of polymers using the vinyl acetate, the carbon stable isotope ratio ($\delta^{13}C$) of the vinyl acetate obtained from the ethylene and/or the acetic acid as a raw material is preferably in the range of −60 to less than −20‰, more preferably in the range of −50 to −22‰, even more preferably in the range of −45 to −25‰, and particularly preferably in the range of −40 to −26‰ so.

C4 plant is plant that perform C4-type photosynthesis, and C4-type photosynthesis is a form of photosynthesis that has a C4 pathway for concentrating carbon dioxide in addition to the carbene-Benson cycle which is a general carbon dioxide reduction cycle in the process of photosynthesis. An enzyme involved in carbon dioxide fixation in the photosynthetic pathway of the C4 plant is phosphoenolpyruvate carboxylase. This enzyme is not inhibited by oxygen, has a high ability to fix carbon dioxide, and is characterized by the presence of well-developed chloroplasts in vascular bundle sheath cells. Examples of typical C4 plant includes corn, sugarcane, cassava, sorghum, pampas grass, guinea grass, rosegrass, prickly pear, foxtail millet, barnyard millet, barnyard grass, broom trees, and the like, and the broom trees are also known as broom grass, Hahakigi tree, and *kochia* green. Such C4 plant can efficiently fix carbon dioxide. Further, C3 plant is less likely to collect carbon dioxide at high temperatures, but C4 plant collects carbon dioxide even at high temperatures. Moreover, C4 plant can fully perform photosynthesis even with a small amount of water. This is a physiological adaptation for plants to cope with harsh climates such as high temperature, dryness, low carbon dioxide, and low nitrogen soil.

When $\delta^{13}C$ is set to −20‰ or more, these C4 plant and mixtures thereof are widely applied as carbon sources, but corn, sugarcane, and cassava are preferable as the carbon sources in terms of production volume and cost.

CAM plant has a photosynthetic system adapted to dry environments, and this photosynthetic system is considered to be a kind of evolved form of C3 photosynthesis. CAM plant includes, for example, Cactaceae, crassulaceae, and Euphorbiaceae. The carbon stable isotope ratio of CAM plant is generally in the range of −35‰ to −10‰, and these CAM plant can be used as raw materials in combination if necessary.

As described above, since the $\delta^{13}C$ of the vinyl acetate mainly depends on the $\delta^{13}C$ of the raw material, $\delta^{13}C$ of the resulting vinyl acetate can be adjusted by appropriately mixing ethylene and/or acetic acid with different carbon isotope ratios. For example, when the vinyl acetate is produced by using ethylene and/or acetic acid obtained from the biomass of C4 and C3 plants and mixing these at a predetermined ratio, the value of $\delta^{13}C$ can be adjusted as appropriate along with the value of $^{14}C$.

In the vinyl acetate polymer and its saponified product, since 65% by mass or more of a main component of the carbon source constituting the vinyl acetate polymer and its saponified product is usually derived from the vinyl acetate although there are trace amounts of cross-linking agents, additives, and graft components that are used as necessary, it is possible to control $\delta^{13}C$ and $^{14}C/C$ of the vinyl acetate polymer obtained from the vinyl acetate and its saponified product by controlling $\delta^{13}C$ and $^{14}C/C$ of the vinyl acetate.

Further, the vinyl acetate of the present invention may be used by mixing two or more kinds of vinyl acetate each having different $^{14}C/C$ and $\delta^{13}C$ within the above range if necessary.

For example, not only the vinyl acetate exhibiting a predetermined $\delta^{13}C$ is obtained by using the raw material derived from C3 plant, but the two or more kinds of vinyl acetate with different $\delta^{13}C$ are mixed to obtain a predetermined $\delta^{13}C$ with a more specific $\delta^{13}C$, that is, $\delta^{13}C$ that cannot be achieved by C3 plant alone, so that the tracing accuracy of the obtained vinyl acetate polymer and its saponified product can be further improved. Specifically, if a different $\delta^{13}C$ raw material is used, a statistical analysis value obtained by analyzing the carbon stable isotope ratio of the raw material will be unique, so that it can be distinguished from other raw materials. Therefore, the vinyl acetate polymer produced from such a raw material and the saponified product thereof also have unique analytical values, facilitating identification and trace.

When the two or more kinds of vinyl acetate having different $\delta^{13}C$ are mixed and used, they may be mixed at a stage of purified vinyl acetate as a final product, or distillation purification may be carried out after mixing the two or more kinds of crude vinyl acetate in the preceding step.

Alternatively, two or more kinds of ethylene having different $\delta^{13}C$ and/or two or more kinds of acetic acid having different $\delta^{13}C$ may be mixed and then reacted to form the vinyl acetate.

Among them, from the viewpoint of adjustment of trace components and diversity of raw materials, and from the viewpoint of further increasing the traceability of the obtained vinyl acetate polymer and its saponified product, a method of using a plurality of raw material sources of fossil raw materials and non-fossil raw materials as the vinyl acetate is preferred. The mixing ratio in the production method may be constant or may be changed for each time or for each vinyl acetate polymer and its saponified product.

In addition, since the vinyl acetate is neither vinyl acetate derived from 100% fossil raw material nor vinyl acetate derived from 100% non-fossil raw material, the obtained vinyl acetate polymer and its saponified product have a unique and specific $^{14}C/C$ so that it is preferable because the tracing accuracy increases. The ratio of non-fossil raw materials and fossil raw materials can be specified by quantifying $^{14}C/C$ for the obtained vinyl acetate polymer and its saponified product.

Furthermore, by using a plurality of raw material sources of fossil raw materials and non-fossil raw materials as vinyl acetate, fluctuations in the raw material cost of the resin obtained can be suppressed. The vinyl acetate polymer obtained from the vinyl acetate and its saponified product are excellent in cost and stability of the raw material source and can be widely used. For example, if bio-ethylene obtained from bioethanol or bio-naphtha is used as the non-fossil raw material for the vinyl acetate and ethylene derived from naphtha is used as the fossil raw material, the above effects can be further expected.

The vinyl acetate having the specific carbon isotope ratio preferably further contains the following compounds.

The vinyl acetate of the present invention preferably contains a sulfur component in an amount of more than 0 ppm and 100 ppm or less. As described above, the vinyl acetate of the present invention can easily control $^{14}C/C$ and $\delta^{13}C$ by using the ethylene and/or the acetic acid derived from the biomass as raw materials. When the ethylene and/or the acetic acid derived from the biomass are used, the vinyl acetate containing an organic sulfur compound derived from the biomass is obtained. On the other hand, since the vinyl acetate derived from the petroleum is desulfurized during cracking of naphtha, it has a lower content of the sulfur component than the vinyl acetate derived from the biomass. Therefore, it becomes easier to trace the vinyl acetate and the vinyl acetate polymer derived from the biomass by comparing the content of the sulfur component. In particular, the vinyl acetate and the vinyl acetate polymer derived from the biomass contain dimethyl sulfide or dimethyl sulfoxide as a sulfur component, so the vinyl acetate with the dimethyl sulfide or the dimethyl sulfoxide is easier to trace.

From the viewpoint that a vinyl alcohol polymer obtained by copolymerizing the vinyl acetate and the ethylene in the presence of an acetate ester and saponifying it has improved melt extrusion stability and excellent hue, the vinyl acetate preferably contains the acetate ester.

When the vinyl acetate is polymerized, an aliphatic alcohol having 4 or less carbon atoms used as a polymerization solvent and the vinyl acetate cause a transesterification reaction, resulting in acetaldehyde produced by the following formula (4):

[Formula 3]

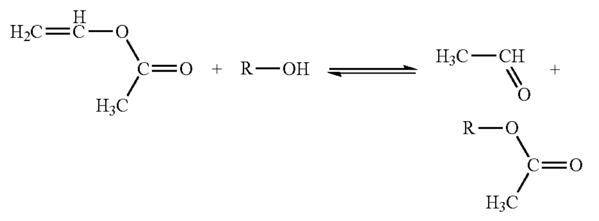

where R is an alkyl group having 4 or less carbon atoms. If a content of the acetaldehyde exceeds 200 ppm, the melt extrusion stability and melt moldability of the vinyl alcohol polymer may deteriorate, and the molded article may be colored and gelled.

Although mechanism of adverse effects caused by the acetaldehyde is not necessarily clear, it is conceivable that the acetaldehyde acts as a chain transfer agent during polymerization and affects the polymerization degree, polymerization degree distribution, branching, or the like of the resulting ethylene-vinyl acetate copolymer so that the melt extrusion stability and melt moldability of the ethylene-vinyl alcohol copolymer are adversely affected. In addition, it is conceivable that the acetaldehyde condenses during the polymerization of the ethylene and the vinyl acetate and changes to a condensate that tends to cause coloration and gelling, and the condensate cannot be removed even in the subsequent purification process of the polymer, so that coloration and gelling are appeared when ethylene-vinyl alcohol copolymer is molded.

Since the transesterification reaction is an equilibrium reaction, an addition of the acetate ester has an effect of suppressing the generation of the acetaldehyde.

As the acetate ester, saturated acetate ester is preferable from the viewpoint of melt extrusion stability and hue. The saturated acetate ester refers to an ester composed of acetic acid and a saturated aliphatic alcohol. The saturated acetate ester is preferably an ester of acetic acid and an aliphatic alcohol having 4 or less carbon atoms, more preferably methyl acetate or ethyl acetate.

A content of the acetate ester with respect to the vinyl acetate is preferably in the range of 10 ppm to 1,500 ppm, more preferably in the range of 30 ppm to 1,300 ppm, even more preferably in the range of 50 ppm to 1,200 ppm, and particularly preferably in the range of 100 ppm to 1,000 ppm.

Further, a plurality of acetate esters may be mixed and used. In this case, it is preferable that a total content of each acetate ester is within the above range.

From the viewpoint of storage stability, the vinyl acetate of the present invention preferably contains a polymerization inhibitor. Examples of the polymerization inhibitor include p-benzoquinone, tert-butylhydroquinone, 4-tert-butylpyrocatechol, cupferron, 2,6-di-tert-butyl-4-methylphenol, N,N-diethylhydroxylamine, hydroquinone, p-methoxyphenol, N-nitroso-N-phenylhydroxylamine aluminum, phenothiazine, tert-butylhydroquinone, dibutylhydroxytoluene, 1,1-diphenyl-2-picrylhydrazyl, and mequinol.

A content of the polymerization inhibitor is preferably in the range of more than 0 ppm and 100 ppm or less, more preferably in the range of more than 0 ppm and 50 ppm or less, even more preferably in the range of more than 0 ppm and 30 ppm or less, and particularly preferably in the range of 1 ppm to 30 ppm. A large amount of the polymerization inhibitor may retard the polymerization rate or cause coloration after production, and if the amount is too small, not only the storage stability of the vinyl acetate may be lowered, but also the polymerization may be slowed down.

From the viewpoint of suppressing the hue of the ethylene-vinyl alcohol copolymer obtained by copolymerizing and saponifying the vinyl acetate and the ethylene and the occurrence of odor and fisheyes during film formation, the vinyl acetate of the present invention preferably contains at least one of a polyvalent carboxylic acid, a hydroxycarboxylic acid and a hydroxylactone-based compound.

Examples of the polyvalent carboxylic acid and the hydroxycarboxylic acid include malonic acid, succinic acid, maleic acid, phthalic acid, oxalic acid, glutaric acid, glycolic acid, lactic acid, glycerin, malic acid, tartaric acid, citric acid, salicylic acid, and the like, and among them, citric acid is preferred.

The hydroxylactone-based compound is not particularly limited as long as it is a compound having a lactone ring and a hydroxyl group in the molecule, but examples of the hydroxylactone-based compound include L-ascorbic acid, erythorbic acid, glucono-delta-lactoic acid, and the like, and among them, L-ascorbic acid and erythorbic acid are preferred.

A content of the polyvalent carboxylic acid, the hydroxycarboxylic acid and the hydroxylactone-based compound with respect to the vinyl acetate is preferably in the range of 1 ppm to 1,000 ppm, more preferably in the range of 5 ppm to 500 ppm, and even more preferably 10 ppm to 300 ppm. When the content of the polyvalent carboxylic acid, the hydroxycarboxylic acid and the hydroxylactone-based compound is less than 1 ppm, the above effect is small, and when it exceeds 1,000 ppm, the polymerization of the vinyl acetate tends to be inhibited.

Examples of a method of adding the polyvalent carboxylic acid, the hydroxycarboxylic acid and the hydroxylactone-based compound include a method of preliminarily adding them to the vinyl acetate, a method of adding them, the vinyl acetate and a solvent simultaneously to the polymerization system at once, a method of adding them to the polymerization system as it is, a method of pre-dissolving them in the solvent used for polymerization and then adding them to the polymerization system, a method of pre-mixing them with other additives and then adding, and a method of dividing and adding them, or the like.

From the viewpoint of controlling a variation in an average polymerization degree of the vinyl acetate polymer and the hue and solubility of the polyvinyl alcohol obtained by saponification, the vinyl acetate of the present invention preferably contains acetaldehyde dimethylacetal.

A content of the acetaldehyde dimethylacetal with respect to the vinyl acetate of 100 parts by mass is preferably in the range of 0.001 to 10 parts by mass, more preferably 0.01 to 7 parts by mass, even more preferably 0.1 to 5 parts by mass, and particularly preferably 1 to 5 parts by mass. If the content of the acetaldehyde dimethylacetal is less than 0.001 parts by mass, the above effect is small, and if it exceeds 10 parts by mass, the polymerization of the vinyl acetate tends to be inhibited.

Examples of a method of adding the acetaldehyde dimethylacetal include a method of preliminarily adding it to the vinyl acetate, a method of adding it, the vinyl acetate and a solvent simultaneously to the polymerization system at once, a method of adding it to the polymerization system as it is, a method of pre-dissolving them in the solvent used for polymerization and then adding it to the polymerization system, a method of pre-mixing it with other additives and then adding, and a method of dividing and adding it, or the like.

By polymerizing or copolymerizing the vinyl acetate of the present invention, a vinyl acetate polymer or copolymer containing the vinyl acetate as a monomer (hereinafter, a polymer and a copolymer may be collectively referred to as a "polymer") can be obtained. In the case of copolymerization, a monomer to be copolymerized may be other monomers copolymerizable with vinyl acetate.

Examples of the other copolymerizable monomers include: ethylene; olefins having 3 to 30 carbon atoms such as propylene, 1-butene and isobutene; acrylic acid or a salt thereof; methyl acrylate, ethyl acrylate, n-propyl acrylate, i-propyl acrylate, n-butyl acrylate, i-butyl acrylate, tert-butyl acrylate, 2-ethylhexyl acrylate, dodecyl acrylate, acrylic acid esters such as octadecyl acrylate; methacrylic acid or its salts; methyl methacrylate, ethyl methacrylate, n-propyl methacrylate, i-propyl methacrylate, n-butyl methacrylate, i-butyl methacrylate, tert-butyl methacrylate, 2-ethylhexyl methacrylate, dodecyl methacrylate, methacrylic acid esters such as octadecyl methacrylate; acrylamide derivatives such as acrylamide, N-methylacrylamide, N-ethylacrylamide, N, N-dimethylacrylamide, diacetoneacrylamide, acrylamide propanesulfonic acid or its salts, acrylamide propyldimethylamine or its salts, N-methylolacrylamide or its derivatives; methacrylamide derivatives such as methacrylamide, N-methylmethacrylamide, N-ethylmethacrylamide, methacrylamide propanesulfonic acid or its salts, methacrylamide propyldimethylamine or its salts, N-methylolmethacrylamide or its derivatives; N-vinylamides such as N-vinylformamide, N-vinylacetamide, N-vinylpyrrolidone; vinyl ethers such as methyl vinyl ether, ethyl vinyl ether, n-propyl vinyl ether, i-propyl vinyl ether, n-butyl vinyl ether, i-butyl vinyl ether, tert-butyl vinyl ether, dodecyl vinyl ether, stearyl vinyl ether; vinyl cyanide such as acrylonitrile, methacrylonitrile; vinyl halides such as vinyl chloride, vinylidene chloride, vinyl fluoride, vinylidene fluoride; allyl compounds such as allyl acetate and allyl chloride; maleic acid or its salts, esters or acid anhydrides; itaconic acid or its salts, esters or anhydrides; vinylsilyl compounds such as vinyltrimethoxysilane; isopropenyl acetate, and the like.

In the polymerization of the vinyl acetate, it is preferable to use an aliphatic alcohol having 4 or less carbon atoms as a polymerization solvent. When aliphatic alcohols having 5 or more carbon atoms or aromatic alcohols are used, the effect of the present invention may not be sufficiently obtained. Examples of the aliphatic alcohol having 4 or less carbon atoms include methanol, ethanol, propanol and butanol, and among them, methanol, ethanol and propanol are preferred, methanol and ethanol are more preferred, and methanol is even more preferred.

As described above, since the vinyl acetate of the present invention has the ratio of carbon-14 to the total carbon of $1.0\times10^{-14}$ or more, the ratio of carbon-14 to the total carbon in the vinyl acetate polymer obtained by polymerizing such vinyl acetate is $1.0\times10^{-14}$ or more.

When vinyl acetate with the carbon stable isotope ratio of −20‰ or more is used as the vinyl acetate, the carbon stable isotope ratio in the obtained vinyl acetate polymer is −20‰ or more. Further, when vinyl acetate having the carbon stable isotope ratio of less than −20‰ is used as the vinyl acetate, the carbon stable isotope ratio in the obtained vinyl acetate polymer is less than −20‰.

When the vinyl acetate contains the sulfur component in the amount of more than 0 ppm and 100 ppm or less, the content of the sulfur component in the obtained vinyl acetate polymer exceeds 0 ppm and is 100 ppm or less. As described above, the contained sulfur component is preferably dimethylsulfide or dimethylsulfoxide from the viewpoint of easy tracing.

A vinyl alcohol polymer is obtained by saponifying the polymer having the vinyl acetate as a monomer unit. As described above, when the vinyl acetate polymer having the ratio of carbon-14 to the total carbon of $1.0\times10^{-14}$ or more is used, the resulting vinyl alcohol polymer has a ratio of carbon-14 to the total carbon of $1.0\times10^{-14}$ or more.

When the vinyl acetate polymer having the carbon stable isotope ratio of −20‰ or more is used as the vinyl acetate polymer, the carbon stable isotope ratio in the resulting vinyl alcohol polymer is −20‰ or more. Further, when the vinyl acetate polymer having the carbon stable isotope ratio of less than −20‰ is used as the vinyl acetate polymer, the carbon stable isotope ratio in the resulting vinyl alcohol polymer is less than −20‰.

When the vinyl acetate contains the sulfur component in the amount of more than 0 ppm and 100 ppm or less, the content of the sulfur component in the resulting vinyl alcohol polymer exceeds 0 ppm and is 100 ppm or less. As described above, the contained sulfur component is preferably dimethylsulfide or dimethylsulfoxide from the viewpoint of easy tracing.

When the polymer having the vinyl acetate as a monomer unit is a copolymer of the vinyl acetate and other monomers that can be copolymerized, a vinyl alcohol polymer containing ethylene units obtained by saponifying a vinyl acetate-ethylene copolymer in which the other copolymerizable monomer is ethylene is preferred. When the vinyl alcohol polymer contains the ethylene units, a content of the ethylene units is preferably in the range of 1 mol% or more and 60 mol% or less, more preferably in the range of 1 mol% or more and 55 mol% or less.

The degree of saponification of the vinyl alcohol polymer is preferably 80 mol% or more, more preferably 85 mol% or more, and even more preferably 90 mol% or more. The degree of saponification means a ratio (mol%) indicating the number of moles of the vinyl alcohol units based on the total number of moles of the structural units (typically, vinyl ester monomer units) that may be converted to vinyl alcohol units by saponification and the vinyl alcohol units in the vinyl alcohol polymer.

The degree of saponification of the vinyl alcohol polymer can be measured according to JIS K 6726: 1994. Specifically, when the degree of saponification is 99.5 mol% or less, for the ethylene-modified vinyl alcohol polymer saponified to the degree of saponification of 99.5 mol% or more, the intrinsic viscosity [q] (liter/g) measured in water at 30° C was used to determine the viscosity-average degree of polymerization (P) according to the following formula.

$$\text{Degree of polymerization } P=([\eta]\times10^{4}/8.29)^{(1/0.62)}$$

From the viewpoint of ensuring sufficient mechanical strength of the obtained film, the degree of polymerization of the vinyl alcohol polymer is preferably 200 or more, more preferably 300 or more, even more preferably 500 or more. Further, from the viewpoint of productivity and water solubility of the vinyl alcohol polymer, the degree of polymerization is preferably 5,000 or less, more preferably 3,000 or less.

The vinyl alcohol polymer preferably has a 1,2-glycol bond. A content of the 1,2-glycol bonds is preferably 0.2 mol% or more, more preferably 0.3 mol% or more, even more preferably 0.4 mol% or more, and particularly preferably 0.5 mol% or more. Further, the content of the 1,2-glycol bond is preferably 2 mol% or less, more preferably 1.5 mol% or less, even more preferably 1.3 mol% or less, and particularly preferably 1.0 mol% or less.

In addition to the ease of tracing, from the viewpoint of the hue of the resulting film and the viscosity stability of the aqueous solution during film formation, the vinyl alcohol polymer of the present invention is preferably a vinyl alcohol polymer containing ethylene units in an amount of 1 mol% or more and 15 mol% or less with respect to total monomer units in the vinyl alcohol polymer, having the degree of saponification in the range of 85 mol% or more and 99.9 mol% or less, and having a propyl group at a terminal end thereof wherein a content of the propyl group with respect to the total monomer units is in the range of 0.0005 mol% or more and 0.1 mol% or less (hereinafter, may be referred to as "ethylene-modified vinyl alcohol polymer").

the viscosity-average degree of polymerization of the ethylene-modified vinyl alcohol polymer is preferably in the range of 200 or more and 3,000 or less, more preferably in the range of 400 or more and 2,800 or less, and even more preferably in the range of 450 or more and 2,500 or less. The viscosity-average degree of polymerization is a value obtained by measuring according to JIS K 6726: 1994, as described above.

The degree of saponification of the ethylene-modified vinyl alcohol polymer is preferably in the range of 80 mol% or more and 99.9 mol% or less, more preferably in the range of 90 mol% or more and 99.9 mol% or less.

The ethylene-modified vinyl alcohol polymer preferably has the propyl group at one terminal end thereof and the content of the propyl group is preferably in the range of 0.0005 mol% or more and 0.10 mol% or less, more preferably in the range of 0.001 mol% or more and 0.08 mol% or less, and even more preferably in the range of 0.005 mol% or more and 0.05 mol% or less.

A method for introducing the propyl group is preferably, for example, a method of reacting the ethylene and the vinyl acetate in the presence of an initiator and a chain transfer agent each having a propyl group in the polymerization step.

By using the initiator and the chain transfer agent each having the propyl group in combination in this manner, the ethylene-modified vinyl alcohol polymer having a specific amount of propyl groups introduced at one terminal end can be efficiently produced.

Examples of the initiator having the propyl group include n-propylperoxydicarbonate, 1,1'-propane-1-nitrile and the like. An amount of the initiator having the propyl group to be used is preferably in the range of 0.000125% by mass or more and 0.25% by mass or less with respect to the vinyl acetate in order to obtain the content of the propyl group within the above range, more preferably in the range of 0.0003% by mass or more and 0.2% by mass or less, and even more preferably in the range of 0.0005% by mass or more and 0.15% by mass or less.

Examples of the chain transfer agent having the propyl group include propanethiol, propylaldehyde and the like. An amount of the chain transfer agent having the propyl group to be used is preferably in the range of 0.0001% by mass or more and 0.005% by mass or less with respect to the vinyl acetate in order to obtain the content of the propyl group within the above range, more preferably in the range of 0.0002% by mass or more and 0.004% by mass or less, and even more preferably in the range of 0.0003% by mass or more and 0.003% by mass or less.

A polymerization temperature is not particularly limited, but is preferably in the range of 0 °C to 180 °C, more preferably in the range of 20 °C to 160 °C, and even more preferably in the range of 30 °C to 150 °C. When polymerizing below the boiling point of the solvent used in the polymerization process, either boiling polymerization under reduced pressure in which the polymerization is carried out while boiling the solvent under reduced pressure or non-boiling polymerization under atmospheric pressure in which the polymerization is carried out while the solvent is not boiled under atmospheric pressure can be selected. Further, when polymerizing above the boiling point of the solvent used in the polymerization process, either non-boiling polymerization under pressure in which the polymerization is carried out while the solvent is not boiled under pressure or boiling polymerization under pressure in which the polymerization is carried out while the solvent is boiled under pressure can be selected.

An ethylene pressure in a polymerization reactor in the polymerization step is not particularly limited, but is preferably in the range of 0.01 MPa to 0.9 MPa, more preferably in the range of 0.05 MPa to 0.7 MPa, and even more preferably in the range of 0.1 MPa to 0.65 MPa.

A polymerization rate of the vinyl acetate at an outlet of the polymerization reactor is not particularly limited, but it is preferably in the range of 10% to 90%, more preferably in the range of 15% to 85%.

For ease of tracing, a content of an alkoxy group of the vinyl alcohol polymer obtained by polymerizing the vinyl acetate of the present invention is preferably in the range of 0.0005 mol% to 1 mol% based on a number of moles of all structural units (total monomer units and units having alkoxy groups) constituting the vinyl alcohol polymer, more preferably 0.0007 mol% or more, and even more preferably 0.001 mol% or more. On the other hand, the content of the alkoxy group is preferably 0.5 mol% or less, more preferably 0.3 mol% or less.

Example of a method for producing the vinyl alcohol polymer containing the alkoxy group include a method of saponifying the vinyl ester polymer obtained by copolymerizing the vinyl acetate of the present invention with an unsaturated monomer having the alkoxy group. The monomer having the alkoxy group is not particularly limited as long as it is an unsaturated monomer having the alkoxy group and copolymerizable with the vinyl ester, and examples of the monomer include alkyl vinyl ether, alkyl allyl ether, N-alkoxyalkyl(meth)acrylamide and the like, and N-alkoxyalkyl(meth)acrylamide is preferred. The monomers having the alkoxy group may be used singly or in combination of two or more, with the former being preferred.

In the case of the vinyl alcohol polymer obtained by polymerizing the vinyl acetate and the ethylene according to the present invention, the vinyl alcohol polymer preferably has a structure (I) represented by a following structural formula (I):

[Formula 4]

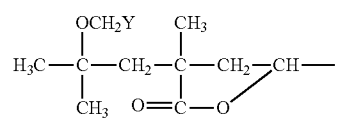

(I)

(where Y is a hydrogen atom or a methyl group.) and a structure (II) represented by a following structural formula (II):

[Formula 5]

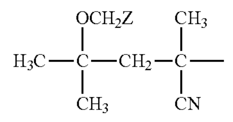

(II)

(where Z is a hydrogen atom or a methyl group.) at a terminal end of the polymer. Further, a total content of the structure (I) and the structure (II) is preferably in the range of 0.001 mol% or more and 0.1 mol% or less with respect to total monomer units. Such a vinyl alcohol polymer is excellent in viscosity stability at an initial stage of melting of the vinyl alcohol polymer in addition to the ease of tracing and can stabilize the melt molding process, and in addition, such a vinyl alcohol polymer is preferable from the viewpoint of color resistance under high temperature such as 80° C. and alkaline conditions. A total content of the structure (I) and the structure (II) is more preferably 0.07 mol% or less, even more preferably 0.05 mol% or less, and particularly preferably 0.02 mol% or less. On the other hand, the total content is more preferably 0.002 mol% or more.

In this specification, the monomer unit in the vinyl alcohol polymer means a vinyl alcohol unit, a vinyl ester unit, an ethylene unit in the case of a copolymer with ethylene, and other monomer units to be copolymerized as necessary, and total monomer units means the total number of moles of each monomer unit. At this time, the unit including the terminal structure represented by the structure (I) or the structure (II) is also included in the monomer unit in the calculation.

Both the structure (I) and the structure (II) are structures derived from the polymerization initiator used in the polymerization step. Among them, the structure (I) contains a cyclic ester structure formed by reaction between a nitrile group derived from a polymerization initiator and a hydroxyl group in the same molecule, and the structure (II) is a structure before such a reaction occurs.

By using an azonitrile-based compound containing an alkoxy group as the polymerization initiator, the structure (I) can be introduced into the polymerization terminal. Examples of the azonitrile-based compound containing the alkoxy group include 2,2'-azobis(4-methoxy-2,4-dimethylvaleronitrile), 2,2'-azobis(4-ethoxy-2,4-dimethylvalero nitrile) and the like, and among them, 2,2'-azobis(4-methoxy-2,4-dimethylvaleronitrile) is preferred. Such azonitrile-based compounds containing the alkoxy group are less likely to undergo abnormal decomposition upon contact with metals and have a high decomposition rate at low temperatures. Therefore, by using the azonitrile-based compound, the ethylene and the vinyl ester can be copolymerized safely, efficiently and economically.

In the vinyl alcohol polymer having the structures (I) and (II) at the terminal end of the polymer, from the viewpoint of hydrophilicity of the vinyl alcohol polymer, a content of ethylene units is preferably in the range of 1 mol% or more and 15 mol% or less, more preferably in the range of 1 mol% or more and 10 mol% or less, even more preferably in the range of 1 mol% or more and 8 mol% or less, and particularly preferably in the range of 1 mol% or more and 5 mol% or less.

In the vinyl alcohol polymer having the structures (I) and (II) at the terminal end of the polymer, from the viewpoint of water resistant adhesive viscosity of the adhesive obtained from the vinyl alcohol polymer, the viscosity-average degree of polymerization is preferably in the range of 200 or more and 3,000 or less, more preferably in the range of 400 or more and 2,800, and even more preferably in the range of 450 or more and 2,500.

Further, in the vinyl alcohol polymer having the structures (I) and (II) at the terminal end of the polymer, from the viewpoint of the solubility in water and the water-resistant adhesion of the adhesive obtained from the vinyl alcohol polymer, the degree of saponification is preferably in the range of 85 mol% or more and 99.9 mol% or less, more preferably in the range of 90 mol% or more and 99.9 mol% or less.

In the vinyl alcohol polymer having the structures (I) and (II) at the terminal end of the polymer, a molar ratio R [I/(I+II)] of the structure (I) to a total of the structure (I) and the structure (II) satisfies a following formula (1). It is preferred that the molar ratio R [I/(I+II)] satisfies a following formula (1-1), it is more preferred that the molar ratio R [I/(I+II)] satisfies a following formula (1-2), and it is even more preferred that the molar ratio R [I/(I+II)]satisfies a following formula (1-3). The molar ratio R[I/(I+II)] can be adjusted by washing the vinyl alcohol polymer after saponification. On the other hand, the molar ratio R[I/(I+II))] is preferably 0.1 or more. This is because it is difficult to make it less than 0.1 in terms of the industrial production method of EVOH, which leads to an increase in production cost.

$$R < 0.92 - Et/100 \quad (1)$$

$$R < 0.90 - Et/100 \quad (1\text{-}1)$$

$$R < 0.88 - Et/100 \quad (1\text{-}2)$$

$$R < 0.85 - Et/100 \quad (1\text{-}3)$$

[In the formulae (1) to (1-3), Et is the content of the ethylene unit (mol%).]

Further, the molar ratio R [I/(I+II)] of the structure (I) to a total of the structure (I) and the structure (II) preferably satisfies a following formula (2), and more preferably satisfies a following formula (2-1).

$$0.8 < R + Et/100 \quad (2)$$

$$0.9 < R + Et/100 \quad (2\text{-}1)$$

[In formulae (2) and (2-1), Et is the same as described above.]

In the above formulae (1) to (1-3), if the molar ratio R [I/(I+II)] does not satisfy the above formula, the water solubility of the ethylene-vinyl alcohol copolymer may be reduced, and when the vinyl alcohol polymer is used as an adhesive, the high-speed coatability of the resulting adhesive may be lowered.

In addition, in the formulae (2) and (2-1), a large value on the right side means that a proportion of the nitrile group derived from the polymerization initiator converted to the cyclic ester structure is high, and the formula (2-1) means that the proportion is even higher. By satisfying the formula (2), the viscosity stability of the vinyl alcohol polymer at the initial stage of melting can be improved, and a rapid increase in viscosity at the initial stage of melting after 5 to 20 minutes from the initiation of melting can be suppressed. When the formula (2-1) is satisfied, such increase in viscosity is further suppressed.

In the case of the vinyl alcohol polymer obtained by polymerizing the vinyl acetate of the present invention and the ethylene, the vinyl alcohol polymer in which a block character of the ethylene units is in the range of 0.90 to 0.99 is preferred. When such a vinyl alcohol polymer is used as a coating material, such a vinyl alcohol polymer is preferable from the viewpoint of the viscosity stability of the resulting coating material and the barrier properties of the resulting coated paper in addition to ease of tracing.

The block character is a numerical value representing distributions of the ethylene unit and the vinyl alcohol unit generated by saponification of the vinyl ester unit and takes a value between 0 and 2. "0" indicates that the ethylene unit or the vinyl alcohol unit is completely distributed in blocks, and as the numerical value increases, the alternation increases. "1" indicates that the ethylene unit and the vinyl alcohol unit are present completely randomly, and "2" indicates that the ethylene unit and the vinyl alcohol unit are present completely alternately.

The block character is determined by $^{13}C$-NMR as follows. First, the ethylene-vinyl alcohol copolymer is saponified to a degree of saponification of 99.9 mol% or more, then thoroughly washed with methanol and dried under reduced pressure at 90 °C for 2 days. After dissolving the obtained fully saponified ethylene-vinyl alcohol copolymer in DMSO-$d_6$, the obtained sample is measured at 80 °C by using 500 MHz $^{13}C$-NMR (JEOL GX-500). From an obtained spectrum chart, using a mole fraction (AE) of vinyl alcohol-ethylene 2-unit chain, a mole fraction (A) of the vinyl alcohol unit and a mole fraction (E) of the ethylene unit assigned and calculated by a method described in T. Moritani and H. Iwasaki, 11, 1251-1259, Macromolecules (1978), a block character (q) of the ethylene unit is obtained from the following formula.

$$\eta = (AE)/\{2 \times (A) \times (E)\}$$

The ethylene-vinyl ester copolymer having the block character can be obtained by contacting with an ethylene-containing gas while stirring a vinyl ester-containing solution by using wide paddle blades in a polymerization tank so that a stirring power Pv per unit volume is in the range of 0.5 to 10 $kW/m^3$ and a Froude number Fr is in the range of 0.05 to 0.2.

As described above, the vinyl acetate of the present invention has a specific $^{14}C/C$ value, unlike vinyl acetate obtained from conventional fossil source ethylene and acetic acid. Further, in addition to $^{14}C/C$, $\delta^{13}C$ also preferably has a value different from that of conventional vinyl acetate. Accordingly, since the vinyl acetate of the present invention, the vinyl acetate polymer having the vinyl acetate as a monomer unit obtained by polymerizing the vinyl acetate, and the vinyl alcohol polymer which is a saponified product thereof have a specific range of $^{14}C/C$, more preferably a specific range of $\delta^{13}C$, these can be distinguished from commercially available or known vinyl acetate, a vinyl acetate polymer obtained by polymerizing vinyl acetate, and saponified products thereof. Therefore, the vinyl acetate polymer and vinyl alcohol polymer obtained using the vinyl acetate of the present invention can be traced after production or after sale.

In the method for tracing the vinyl acetate polymer and the vinyl alcohol polymer after production, $^{14}C/C$ of the vinyl acetate as a raw material before polymerization used in the production of the vinyl acetate polymer and its saponified product, the vinyl alcohol polymer, is analyzed and recorded in advance. By measuring the $^{14}C/C$ of the vinyl acetate polymer or the vinyl alcohol polymer collected after production or after sale, and comparing the result with the $^{14}C/C$ of the raw material vinyl acetate measured in advance, it is possible to determine whether or not the recovered vinyl acetate polymer or the vinyl alcohol polymer is the in-house product, and if it is the in-house product, a lot thereof can be specified. Furthermore, by setting $\delta^{13}C$ within a certain range, these determinations become easier.

In addition to the above, when the vinyl acetate of the present invention contains at least one of the acetate ester, the polymerization inhibitor, the polyvalent carboxylic acid, the hydroxycarboxylic acid, the hydroxylactone-based compound and the acetaldehyde dimethylacetal within the above range, tracing becomes easier.

Further, when the vinyl alcohol polymer obtained by polymerizing the vinyl acetate of the present invention and saponifying the vinyl acetate polymer containing the vinyl acetate of the present invention as a monomer unit contains at least one of the 1,2-glycol bond, the propylene group or the alkoxy group at the terminal end of the polymer, the structure (I) and the structure (II), and block characters within the above range, along with being easy to trace, the properties of the obtained vinyl alcohol polymer are improved, and it can be suitably used for the intended use.

In addition to measuring $^{14}C/C$ and $\delta^{13}C$ of products collected after use, by measuring at least one of the 1,2-glycol bond, the propylene group or the alkoxy group at the terminal end of the polymer, the structure (I) and the structure (II), and the block character by the above method, it is possible to determine whether or not the collected product contains the in-house vinyl alcohol polymer, as well as the production line.

As described above, the raw materials can be traced from the vinyl acetate polymer having the vinyl acetate of the present invention as a monomer unit and the vinyl alcohol polymer which is a saponified product thereof so that the quality of the molded article obtained from the vinyl acetate polymer or the vinyl alcohol polymer can be fed back to the quality of the raw material vinyl acetate. In addition, it becomes possible to easily investigate the production line of the vinyl acetate polymer or the vinyl alcohol polymer, which is the raw material of the molded product, and the vinyl acetate.

In the above description, substances, conditions, methods, numerical ranges, and the like are exemplified, but the present invention is not limited to such exemplifications. Specifically, the present invention is not limited to each embodiment, and can be modified in various ways within the scope of the claims and can be obtained by appropriately combining technical means disclosed in different embodiments. Any embodiment is also included in the technical scope of the present invention. In addition, the exemplified substances may be used singly or in combination of two or more unless otherwise noted.

EXAMPLES

The present invention will be described in more detail below with reference to examples, but the present invention is not limited to these examples. Measurements and evaluations in the following examples were carried out according to the following methods.

(1) Analysis of Vinyl Acetate

Using gas chromatography, 1 g of n-propyl acetate was added as an internal standard to 6 g of a reaction solution, and this was used as an analysis solution. The measurement conditions were as follows.

Apparatus: GC-9A manufactured by Shimadzu Corporation

Detector: FID

Column: TC-WAX manufactured by GL Sciences Co., Ltd. (length 30 m, inner diameter 0.25 mm, film thickness 0.5 μm)

Injection temperature: 200 °C

Detector temperature: 200 °C

Column temperature: raised from 45 °C (held for 2 minutes) to 130 °C at a heating rate of 4 °C/min and held for 15 minutes, then raised to 200 °C at a heating rate of 25 °C/min and held for 10 minutes.

(2) Measurement of Carbon Isotope Ratio

A sample was converted to carbon dioxide using a pretreatment method (ASTM D6866/Method B) specified by the American Society of Testing and Materials. After that, it was graphitized by a complete reduction treatment using an iron catalyst, and the carbon stable isotope ratio ($\delta^{13}C$) was determined by Accelerator Mass Spectrometry. As for a calculation formula, $\delta^{13}C$ is obtained by the above formula (3).

Graphite synthesized from an oxalic acid reference substance (HOxII) provided by the US National Institute of Standards and Technology was used as a $^{14}C$ concentration standard. The carbon isotope ratios ($^{14}C/^{12}C$ ratio, $^{13}C/^{12}C$ ratio) of the sample and the standard were measured by Accelerator Mass Spectrometry, and the $^{14}C$ concentration was calculated from measurement results. Using a $^{14}C$ concentration of the sample obtained by measurement, a mixing ratio of biomass-derived carbon and fossil resource-derived carbon was evaluated for carbon contained in the sample.

(3) Measurement of Content of Sulfur Component

A content of sulfur component was quantified using a trace nitrogen sulfur analyzer (TS-2100H type) manufactured by Mitsubishi Analytech, and measurement conditions were as follows.

Heater temperature: Inlet 900 °C, Outlet 900 °C
Gas flow rate: Ar, O2 300 ml/min each
[Analysis system NSX-2100]
Measurement mode: TS
Parameter: SD-210
Measurement time (timer): 540 seconds (9 minutes)
PMT sensitivity: high concentration (4) The content of the sulfur component was identified using gas chromatography (GC) and gas chromatography mass spectrometry (GC/MS). As a GC detector, an FPD (Flame Photometric Detector), which exhibits high sensitivity to trace amounts of sulfur compounds and phosphorus compounds, is used, and identification was carried out by analyzing mass components observed at retention times when the sulfur component was detected.

(5) Degree of Saponification and average degree of polymerization of vinyl alcohol polymer A methanol solution of polyvinyl acetate obtained by removing unreacted vinyl acetate monomer after polymerization was saponified at an alkali molar ratio of 0.5, and then a pulverized product was allowed to stand at 60 °C for 5 hours to promote saponification. Thereafter, methanol Soxhlet treatment was carried out for 3 days, followed by vacuum drying at 80 °C for 3 days to obtain a purified vinyl alcohol polymer. A degree of saponification and an average degree of polymerization of this purified vinyl alcohol polymer were measured according to JIS K6726: 1994.

(6) Content of ethylene unit and saponification degree of ethylene-vinyl alcohol copolymer Ethylene-vinyl alcohol copolymer pellets are dissolved in dimethyl sulfoxide (DMSO)-$d_6$ containing tetramethylsilane as an internal standard substance and tetrafluoroacetic acid as an additive and measured by using 1H-NMR at 500 MHz (manufactured by JEOL Ltd. "JMTC-400/54/SS") at 80 °C to determine the ethylene unit content and degree of saponification.

Each peak in the spectrum of the measurement is assigned as follows.

0.6 to 1.9 ppm: methylene proton (4H) of ethylene unit, methylene proton (2H) of vinyl alcohol unit, methylene proton (2H) of vinyl acetate unit
1.9 to 2.0 ppm: methyl proton (3H) of vinyl acetate unit
3.1 to 4.2 ppm: methine proton (1H) of vinyl alcohol unit (7) Quantification of Carboxylic Acid 20 g of ethylene-vinyl alcohol copolymer pellets and 100 mL of ion-exchanged water were put into a 200 mL conical flask with a common stopper, attached with a cooling condenser, and stirred and extracted at 95 °C for 6 hours. The resulting extract was subjected to neutralization titration with an N/50 sodium hydroxide aqueous solution using phenolphthalein as an indicator, and the content of carboxylic acid converted to carboxylic acid group was quantified. When a phosphorus compound was included, the content of carboxylic acid was calculated taking into consideration a content of the phosphorus compound measured by the evaluation method described later.

(8) Quantification of Metal Ion, Phosphorus Compound and Boron Compound 0.5 g of ethylene-vinyl alcohol copolymer pellets were placed in a Teflon (registered trademark) pressure vessel, and 5 mL of concentrated nitric acid was added thereto to decompose at room temperature for 30 minutes. After 30 minutes, a lid was closed, and decomposition was performed by heating at 150 °C for 10 minutes and then at 180 °C for 5 minutes using a wet decomposition apparatus ("MWS-2" manufactured by Actac Co.), and then cooled to room temperature. After cooling, the liquid was transferred to a 50 mL volumetric flask (manufactured by TPX) and diluted with pure water. This solution was subjected to elemental analysis using an ICP emission spectrometer ("OPTIMA4300DV" manufactured by PerkinElmer), and a metal atom equivalent amount of a metal ion, a phosphorus atom equivalent amount of a phosphorus compound and a boron atom equivalent amount of a boron compound contained in the ethylene-vinyl alcohol copolymer pellets were determined.

(9) Oxygen Permeability

Using a single screw extruder ("D2020" manufactured by Toyo Seiki Seisakusho Co., Ltd.; D(mm)=20, L/D=20, compression ratio=3.0, screw: full flight), a monolayer film having an average thickness of 20 μm was produced from the ethylene-vinyl alcohol copolymer pellets. Each condition at this time is as shown below. After conditioning the obtained film under conditions of 20 °C/65% RH, oxygen permeability was measured under conditions of 20 °C/65% RH using an oxygen permeability measuring device ("OX-Tran 2/20" manufactured by Modern Control). The measurement was carried out according to JIS K 7126-2 (isobaric method; 2006) ISO14663-2 annex C.

(Single Screw Extruder Conditions)
Extrusion temperature: 210 °C
Screw rotation speed: 40 rpm
Dice width: 30 cm
Take-up roll temperature: 80 °C
Take-up roll speed: 3.1 m/min

(10) Appearance Evaluation (10-1) Defect Evaluation for Single-Layer Film Formation A single-layer film was produced by continuous operation under the same conditions as above, and a number of defects per film length of 17 cm was counted for each film produced 5 hours after start of operation. The number of defects was counted using a film defect inspection apparatus ("AI-10" manufactured by Frontier System Co., Ltd.). In this regard, a detection camera in this film defect inspection apparatus was installed so that a lens position thereof was at a distance of 195 mm from a film surface.

(10-2) Evaluation of Coloration of Roll End

A roll was produced by winding 100 m of the film produced 5 hours after the start of operation on a paper tube, and presence or absence of coloring due to yellowing at an end of the roll was visually determined.

(11) Amount of 1,2-Glycol Bond

A vinyl alcohol polymer was dissolved in dimethyl sulfoxide (DMSO)-$d_6$ containing tetramethylsilane as an internal standard substance and tetrafluoroacetic acid as an additive and measured by using $^1$H-NMR at 500 MHz (manufactured by JEOL Ltd. "JMTC-400/54/SS") at 80 °C. A peak derived from the methine proton of the vinyl alcohol unit is assigned from 3.2 to 4.0 ppm (integral value A), and a peak derived from one methine proton of the 1,2-glycol bond is assigned from 3.15 to 3.35 ppm (integral value B). An amount of the 1,2-glycol bond is calculated by a following formula.

$$\text{Amount of 1,2-glycol bond(mol\%)}=B/A\times 100$$

(12) Content of Propyl Group at One Terminal End

A content of a propyl group at one terminal end of the vinyl alcohol polymer was obtained from $^1$H-NMR of the vinyl ester polymer, which is a precursor or re-acetate of the vinyl alcohol polymer. After performing reprecipitation purification of the sample ethylene-modified vinyl ester polymer three times or more using a mixed solution of n-hexane and acetone, the sample was dried under reduced pressure at 80 °C for 3 days to prepare an ethylene-modified vinyl ester polymer for analysis. The ethylene-modified vinyl ester polymer for analysis was dissolved in DMSO-$d_6$ and measured using $^1$H-NMR at 500 MHz (manufactured by JEOL Ltd. "JMTC-400/54/SS") at 80° C. Using a peak derived from a main chain methine proton of the vinyl acetate (integral value R: 4.7 to 5.2 ppm) and a peak derived from a methyl proton of the propyl group (integral value S: 0.7 to 1.0 ppm), a content of the propyl group is calculated by a following formula.

$$\text{Content of propyl group (mol\%)}=100\times(S/3)/R$$

(13) Content of Sodium Acetate in Resin Material

A content of sodium acetate in a resin material mainly composed of the vinyl alcohol polymer is determined according to the dissolution conductivity method described in JIS K 6726: 1994.

(14) Solubility of Resin Material 90 g of water per 10 g of the resin material, that is, 100 g of a 10% aqueous solution of the resin material is stirred at 90 °C and 300 rpm for 5 hours and then filtered through a wire mesh of 200 mesh. Note that 200 mesh corresponds to a mesh size of 75 μm in terms of JIS standard sieve mesh. The mesh size of the sieve is determined according to the nominal mesh size W of JIS Z 8801-1-2006. A weight of the wire mesh before filtration is defined as a (g). The aqueous solution was dried together with the wire mesh at 105 °C for 3 hours. Total mass of the wire mesh after drying and a material remaining on the wire mesh is defined as b (g). The solubility (%) of the resin material is obtained using a following formula.

$$\text{Solubility (\%)} = 100 - 100\times\{(b\text{-}a)/10\}$$

(15) Viscosity Stability of Aqueous Solution of Resin Material 100 g of the 10% aqueous solution of the resin material prepared under the above conditions was allowed to stand at 5 °C, and a viscosity c was determined when the liquid temperature reached 5 °C. The viscosity c was compared with a viscosity d when the aqueous solution was left at 5 °C for 48 hours, and the viscosity stability of the aqueous solution was obtained from the ratio (viscosity ratio) d/c. The larger the d/c value, the greater the increase in viscosity when left at 5 °C, meaning that the viscosity stability is poor. The viscosity (mPa·s) is a value measured using a Brookfield viscometer ("BLII" manufactured by Toki Sangyo Co., Ltd.) under conditions of a rotor speed of 60 rpm and a temperature of 20 °C.

(16) Hue (YI) of Resin Material

A hue of the resin material was obtained from the yellow index (YI) of the powder. After removing particles less than 100 μm and more than 1,000 μm using a sieve (opening: 100 μm, 1,000 μm), it was measured using a color meter ("SM-T-H1" manufactured by Suga Test Instruments Co., Ltd.). In this regard, YI is a value measured and calculated according to JIS Z 8722: 2009 and JIS K 7373: 2006.

(17) Contents of Structures (I) and (II)

The vinyl alcohol polymer was dissolved in dimethyl sulfoxide (DMSO)-$d_6$ containing tetramethylsilane as an internal standard substance and tetrafluoroacetic acid as an additive and measured by $^1$H-NMR at 500 MHz (manufactured by JEOL Ltd. "JMTC-400/54/SS") at 45 °C. Contents of the structures (I) and (II) were obtained from a ratio of peak intensities of the ethylene unit, the vinyl alcohol unit and the vinyl ester unit to a peak intensity of methyl hydrogen of a methoxy group or methylene hydrogen of an ethoxy group of the structures (I) and (II). In this regard, the peak of the methyl hydrogen of the methoxy group or the methylene hydrogen of the ethoxy group in the structure (I) and the peak of the methyl hydrogen of the methoxy group or the methylene hydrogen of the ethoxy group in the structure (II) were detected around 3.07 ppm and 3.09 ppm, respectively.

(18) Block Character of Ethylene Unit of Ethylene-Vinyl Alcohol Copolymer

The ethylene-vinyl alcohol copolymer is dissolved in dimethyl sulfoxide (DMSO)-$d_6$ containing tetrafluoroacetic acid as an additive and measured by $^{13}$C-NMR at 500 MHz ("JMTC-400/54/SS" manufactured by JEOL Ltd.) at 80 °C. From an obtained spectrum chart, using a mole fraction (AE) of vinyl alcohol-ethylene 2-unit chain, a mole fraction (A) of the vinyl alcohol unit and a mole fraction (E) of the ethylene unit assigned and calculated by a method described in T. Moritani and H. Iwasaki, 11, 1251-1259, Macromolecules (1978), a block character (q) of the ethylene unit was obtained from the following formula.

$$\eta=(AE)/\{2\times(A)\times(E)\}$$

<Synthesis Example 1: Preparation of Vinyl Acetate Synthesis Catalyst>

A silica spherical carrier is impregnated with an aqueous solution containing an aqueous solution of sodium tetrachloropalladate and an aqueous solution of tetrachloroauric acid tetrahydrate corresponding to a water absorption amount of the carrier, immersed in an aqueous solution containing sodium metasilicate nonahydrate, and allowed to stand. Subsequently, an aqueous solution of hydrazine hydrate is added, and the mixture is allowed to stand at room temperature, washed with water until chloride ions disappear from the water, and dried. Then, the palladium/gold/support composition is immersed in an acetic acid aqueous solution and allowed to stand. Then, it is washed with water and dried. Then, it is impregnated with an aqueous solution of potassium acetate corresponding to an amount of water absorbed by the carrier and dried to obtain a vinyl acetate synthesis catalyst.

<Synthesis Example 2: Production of Bio-Ethylene Derived from Rice Straw>

Bioethanol is obtained by treating rice straw, which is C3 plant, as a raw material through an alkali treatment process, a saccharification process, and an ethanolization process. By subjecting this bioethanol to a dehydration reaction treatment at 190° C. using mordenite as a catalyst, bio-ethylene derived from C3 plant can be obtained.

<Synthesis Example 3: Production of Bio-Acetic Acid Derived from Rice Straw>

By oxidizing the bioethanol obtained in Synthesis Example 2, bio-acetic acid derived from C3 plant can be obtained.

Example 1

The catalyst obtained in Synthesis Example 1 was diluted with glass beads and filled in a SUS reaction tube, and a mixed gas of ethylene, oxygen, water, acetic acid, and nitrogen was passed through to carry out the reaction. The ethylene used was bio-ethylene derived from sugarcane which is C4 plant (manufactured by Braskem SA). Further, acetic acid was introduced into a reaction system as steam after vaporizing bio-acetic acid derived from sugarcane which is C4 plant. A yield and selectivity of the vinyl acetate were obtained by analyzing a reaction outlet gas. The obtained vinyl acetate was analyzed by the method described above to measure $^{14}C/C$, $\delta^{13}C$ and the content of the sulfur component. The obtained vinyl acetate was named VAM-1, and the results are shown in Table 1.

Example 2

The reaction was carried out in the same manner as in Example 1, except that the total amount of the bio-acetic acid was changed to the acetic acid derived from petroleum. The yield and selectivity of the vinyl acetate were obtained by analyzing the reaction outlet gas. The obtained vinyl acetate was analyzed by the method described above to measure $^{14}C/C$, $\delta^{13}C$ and the content of the sulfur component. The obtained vinyl acetate was named VAM-2, and the results are shown in Table 1.

Example 3

The reaction was carried out in the same manner as in Example 1, except that half of the bio-ethylene was changed to the ethylene derived from the petroleum, and the total amount of the bio-acetic acid was changed to the acetic acid derived from the petroleum. The yield and selectivity of the vinyl acetate were obtained by analyzing the reaction outlet gas. The obtained vinyl acetate was analyzed by the method described above to measure $^{14}C/C$, $\delta^{13}C$ and the content of the sulfur component. The obtained vinyl acetate was named VAM-3, and the results are shown in Table 1.

Example 4

The reaction was carried out in the same manner as in Example 1, except that the total amount of the bio-ethylene was changed to the C3 plant-derived ethylene obtained in Synthesis Example 2, and the total amount of the bio-acetic acid was changed to the C3 plant-derived acetic acid obtained in Synthesis Example 3. The yield and selectivity of the vinyl acetate were obtained by analyzing the reaction outlet gas. The obtained vinyl acetate was analyzed by the method described above to measure $^{14}C/C$, $\delta^{13}C$ and the content of the sulfur component. The obtained vinyl acetate was named VAM-4, and the results are shown in Table 1.

Example 5

The reaction was carried out in the same manner as in Example 1, except that the total amount of the bio-ethylene was changed to the C3 plant-derived ethylene obtained in Synthesis Example 2, and the total amount of the bio-acetic acid was changed to the acetic acid derived from the petroleum. The yield and selectivity of the vinyl acetate were obtained by analyzing the reaction outlet gas. The obtained vinyl acetate was analyzed by the method described above to measure $^{14}C/C$, $\delta^{13}C$ and the content of the sulfur component. The obtained vinyl acetate was named VAM-5, and the results are shown in Table 1.

Example 6

The reaction was carried out in the same manner as in Example 1, except that half of the bio-ethylene was changed to the C3 plant-derived ethylene obtained in Synthesis Example 2, the remaining half was changed to the ethylene derived from the petroleum, and the entire amount of bio-acetic acid was changed to the acetic acid derived from the petroleum. The yield and selectivity of the vinyl acetate were obtained by analyzing the reaction outlet gas. The obtained vinyl acetate was analyzed by the method described above to measure $^{14}C/C$, $\delta^{13}C$ and the content of the sulfur component. The obtained vinyl acetate was named VAM-6, and the results are shown in Table 1.

Comparative Example 6

The reaction was carried out in the same manner as in Example 1, except that the total amount of the bio-ethylene was changed to the ethylene derived from the petroleum and the total amount of the bio-acetic acid was changed to the acetic acid derived from the petroleum. The yield and selectivity of the vinyl acetate were obtained by analyzing the reaction outlet gas. The obtained vinyl acetate was analyzed by the method described above to measure $^{14}C/C$, $\delta^{13}C$ and the content of the sulfur component. The obtained vinyl acetate was named VAM-C1, and the results are shown in Table 1.

TABLE 1

| | Ethylene | Acetic acid | Space-time yield [g/L-catalyst · hour] | Selectivity [%] | $^{14}C/C$ [—] | $\delta^{13}C$ [‰] | S [ppm] |
|---|---|---|---|---|---|---|---|
| Example 1 | 100% derived from sugarcane (C4 plant) | 100% derived from sugarcane (C4 plant) | 740 | 90.0 | $9.5 \times 10^{-13}$ | −12 | 1.2 |
| Example 2 | 100% derived from sugarcane (C4 plant) | 100% derived from petroleum | 749 | 90.3 | $5.0 \times 10^{-13}$ | −20 | 0.7 |
| Example 3 | 50% derived from sugarcane (C4 plant)/50% derived from petroleum | 100% derived from petroleum | 747 | 90.1 | $2.4 \times 10^{-13}$ | −22 | 0.3 |
| Example 4 | 100% derived from rice straw (C3 plant) | 100% derived from rice straw (C3 plant) | 748 | 90.2 | $9.5 \times 10^{-13}$ | −38 | 1 |
| Example 5 | 100% derived from rice straw (C3 plant) | 100% derived from petroleum | 745 | 90.2 | $5.1 \times 10^{-13}$ | −32 | 0.6 |
| Example 6 | 50% derived from rice straw | 100% derived from petroleum | 746 | 90.0 | $2.5 \times 10^{-13}$ | −28 | 0.3 |

TABLE 1-continued

| | Ethylene | Acetic acid | Space-time yield [g/L-catalyst · hour] | Selectivity [%] | $^{14}C/C$ [—] | $\delta^{13}C$ [‰] | S [ppm] |
|---|---|---|---|---|---|---|---|
| | (C3 plant)/50% derived from petroleum | | | | | | |
| Comparative Example 1 | 100% derived from petroleum | 100% derived from petroleum | 749 | 90.3 | $<1.0 \times 10^{-14}$ | −25 | <0.01 |

In Table 1, S is the content of the sulfur component in the vinyl acetate.

The vinyl acetate obtained by the method described in Examples 1 to 6 contained dimethylsulfide and/or dimethylsulfoxide as the sulfur component.

Reference Example 1

3 ppm of hydroquinone was added as a polymerization inhibitor to the vinyl acetate (VAM-1) obtained in Example 1.

Reference Example 2

15 ppm of hydroquinone was added as a polymerization inhibitor to the vinyl acetate (VAM-1) obtained in Example 1.

Example 7

720 parts by mass of the vinyl acetate (VAM-1) obtained in Example 1 and 280 parts by mass of methanol were charged into a reactor equipped with a stirrer, a reflux condenser, a nitrogen inlet tube and an addition port for a polymerization initiator, and an inside of the reactor was replaced with nitrogen for 30 minutes while nitrogen bubbling was performed. Heating of the reactor was started, and when the internal temperature reached 60 °C, 0.13 parts by mass of 2,2'-azobisisobutyronitrile was added to initiate polymerization. After polymerizing at 60 °C for 3 hours, the polymerization was stopped by cooling. Subsequently, unreacted vinyl acetate was removed at 30 °C under reduced pressure while occasionally adding methanol to obtain a methanol solution of a vinyl acetate polymer. Next, 9.2 parts by mass of a methanol solution having a sodium hydroxide concentration of 10% by mass was added to the methanol solution of the vinyl acetate polymer prepared by further adding methanol to this methanol solution, and saponification was performed at 40 °C. About 15 minutes after the addition of the methanol solution of sodium hydroxide, a gel-like substance was formed. This gel-like substance was pulverized with a pulverizer, left at 40 °C for 1 hour to promote the saponification, and then 500 parts of methyl acetate was added to neutralize the remaining alkali. After confirming the completion of neutralization using a phenolphthalein indicator, the mixture was separated by filtration to obtain a white solid. 2,000 parts of methanol was added to this white solid, and the mixture was left standing at room temperature for 3 hours for washing. After repeating this washing operation three times, the white solid obtained by centrifugal deliquoring was heat-treated in a dryer at 120 °C for 4.5 hours to obtain a vinyl alcohol polymer (PVOH-1). Table 2 shows the physical properties of PVOH-1.

Example 8

The reaction was carried out in the same manner as in Example 7 to obtain a vinyl alcohol polymer (PVOH-2), except that the total amount of the vinyl acetate was changed to VAM-2. Table 2 shows the physical properties of PVOH-2.

Example 9

The reaction was carried out in the same manner as in Example 7 to obtain a vinyl alcohol polymer (PVOH-3), except that the total amount of the vinyl acetate was changed to VAM-3. Table 2 shows the physical properties of PVOH-3.

Example 10

The reaction was carried out in the same manner as in Example 7 to obtain a vinyl alcohol polymer (PVOH-4), except that half of the vinyl acetate was changed to VAM-1 and the other half was changed to VAM-C1. Table 2 shows the physical properties of PVOH-4.

Example 11

The reaction was carried out in the same manner as in Example 7 to obtain a vinyl alcohol polymer (PVOH-5), except that the total amount of the vinyl acetate was changed to VAM-4. Table 2 shows the physical properties of PVOH-5.

Example 12

The reaction was carried out in the same manner as in Example 7 to obtain a vinyl alcohol polymer (PVOH-6), except that the total amount of the vinyl acetate was changed to VAM-5. Table 2 shows the physical properties of PVOH-6.

Example 13

The reaction was carried out in the same manner as in Example 7 to obtain a vinyl alcohol polymer (PVOH-7), except that the total amount of the vinyl acetate was changed to VAM-6. Table 2 shows the physical properties of PVOH-7.

Example 14

The reaction was carried out in the same manner as in Example 7 to obtain a vinyl alcohol polymer (PVOH-8), except that half of the vinyl acetate was changed to VAM-4 and the other half was changed to VAM-C1. Table 2 shows the physical properties of PVOH-8.

Comparative Example 2

The reaction was carried out in the same manner as in Example 4 to obtain a vinyl alcohol polymer (PVOH—C1), except that the total amount of the vinyl acetate was changed to VAM-C1. Table 2 shows the physical properties of PVOH—C1.

TABLE 2

| | Vinyl acetate | Viscosity-average degree of polymerization | Degree of saponification [mol %] | 0.1% aqueous solution surface tension [dyne/cm] | $^{14}C/C$ [—] | $\delta^{13}C$ [‰] |
|---|---|---|---|---|---|---|
| Example 7 | VAM-1 | 1,616 | 99.6 | 64.7 | $9.5 \times 10^{-13}$ | −12 |
| Example 8 | VAM-2 | 1,626 | 99.7 | 64.9 | $9.5 \times 10^{-13}$ | −13 |
| Example 9 | VAM-3 | 1,650 | 99.7 | 65.3 | $5.0 \times 10^{-13}$ | −19 |
| Example 10 | VAM-1/VAM-C1 = 50/50 | 1,630 | 99.6 | 64.9 | $5.0 \times 10^{-13}$ | −20 |
| Example 11 | VAM-4 | 1,620 | 99.7 | 64.9 | $9.5 \times 10^{-13}$ | −38 |
| Example 12 | VAM-5 | 1,642 | 99.7 | 65.2 | $9.5 \times 10^{-13}$ | −38 |
| Example 13 | VAM-6 | 1,631 | 99.6 | 64.8 | $5.0 \times 10^{-13}$ | −32 |
| Example 14 | VAM-4/VAM-C1 = 50/50 | 1,628 | 99.7 | 64.7 | $5.0 \times 10^{-13}$ | −31 |
| Comparative Example 2 | VAM-C1 | 1,690 | 99.7 | 65.2 | $<1.0 \times 10^{-14}$ | −25 |

As is clear from Table 2 above, even the vinyl acetates with different $^{14}C/C$ and $\delta^{13}C$ can be polymerized and saponified under the same conditions to obtain vinyl alcohol polymers with the same physical properties.

Example 15

Production of Ethylene-Vinyl Acetate Copolymer 105 kg of VAM-1 and 32.3 kg of methanol were charged into a 250 L pressurized reactor equipped with a jacket, a stirrer, a nitrogen inlet, an ethylene inlet, and an initiator addition port, heated to 65° C., and then nitrogen bubbling was performed for 30 minutes to replace an inside of the reactor with nitrogen. Then, ethylene was introduced under pressure so that the reactor pressure (ethylene pressure) was 3.67 MPa. The ethylene derived from sugarcane (manufactured by Braskem SA) was used. After adjusting the temperature in the reactor to 65 °C, 16.8 g of 2,2'-azobis(2,4-dimethylvaleronitrile) as an initiator was put into the methanol solution to initiate polymerization. The ethylene pressure was maintained at 3.67 MPa and the polymerization temperature at 65 °C during the polymerization. After 3 hours, when the polymerization rate of the vinyl acetate reached 45%, the mixture was cooled to terminate the polymerization. After the reactor was opened to remove ethylene, nitrogen gas was bubbled through to completely remove ethylene. After removing unreacted vinyl acetate under reduced pressure, methanol was added to the obtained ethylene-vinyl acetate copolymer to obtain a 20% by mass methanol solution.

(Saponification and Washing)

250 kg of the obtained 20% by mass methanol solution of the ethylene-vinyl acetate copolymer jacket was charged into a 500 L reactor equipped with a stirrer, a nitrogen inlet, a reflux condenser and a solution addition port, and then the solution was heated to 60 °C while nitrogen was blown thereinto, and then 4 kg of sodium hydroxide was added as a methanol solution having a concentration of 2N. After the addition of sodium hydroxide was completed, the system was stirred for 2 hours while maintaining the temperature of the system at 60 °C to advance the saponification reaction. After 2 hours had passed, 4 kg of sodium hydroxide was again added in the same manner, and heating and stirring were continued for 2 hours. Thereafter, 14 kg of acetic acid was added to stop the saponification reaction, and 50 kg of ion-exchanged water was added. While heating and stirring, methanol and water were distilled out of the reactor to concentrate the reaction liquid. After 3 hours, 50 kg of deionized water was added to precipitate an ethylene-vinyl alcohol copolymer. The precipitated ethylene-vinyl alcohol copolymer was collected by decantation and pulverized with a mixer. The obtained ethylene-vinyl alcohol copolymer (EVOH-1) powder was put into an acetic acid aqueous solution of 1 L of water (1 g/L) per 1 g of acetic acid (bath ratio: 20, ratio of 10 kg of powder to 200 L of deionized water) and washed with stirring for 2 hours. This was deliquored, further put into a 1 g/L acetic acid aqueous solution (bath ratio: 20) and washed with stirring for 2 hours. And then, the deliquored product was put into the ion-exchanged water (bath ratio: 20), stirred and washed for 2 hours, and the deliquoring operation was repeated three times for purification. By drying this at 60° C. for 16 hours, a crude dried product of EVOH-1 was obtained.

(Production of Hydrous Pellets)

25 kg of the resulting crude dried EVOH-1 was charged into a 100 L stirring tank equipped with a jacket, a stirrer and a reflux condenser, 20 kg of water and 20 g of methanol were added thereto, and the temperature was raised to 70 °C to dissolve. This solution is extruded through a glass tube with a diameter of 3 mm into a mixed solution of water/methanol=90/10 at a mass ratio cooled to 5 °C to precipitate strands and this strand was cut into pellets with a strand cutter to obtain hydrous pellets of EVOH-1. The hydrous pellets of EVOH-1 were put into an acetic acid aqueous solution having a concentration of 1 g/L (bath ratio: 20) and washed with stirring for 2 hours. This was deliquored, further put into a 1 g/L acetic acid aqueous solution (bath ratio: 20) and washed with stirring for 2 hours. After deliquoring, the aqueous acetic acid solution was renewed and the same operation was performed. After washing with an acetic acid aqueous solution and then deliquoring, the product is put into the ion-exchanged water (bath ratio: 20), stirred and washed for 2 hours, and deliquoring is repeated three times for purification so that hydrous pellets of EVOH-1 were obtained from which the catalyst residue during the saponification reaction and the methanol used during strand precipitation were removed. The moisture content of the resulting hydrous pellets of EVOH-1 was measured with a halogen moisture meter "HR73" manufactured by Mettler.

(Manufacturing of Pellets)

The obtained hydrous pellets of EVOH-1 were put into an aqueous solution (bath ratio 20) containing sodium acetate, acetic acid, concentrated phosphoric acid and boric acid and immersed for 4 hours with periodic stirring. The concentration of each component was adjusted so that the content of each component in the obtained EVOH-1 pellets was as shown in Table 3. By deliquoring after immersion and drying in air at 80 °C for 3 hours and in air at 130 °C for 7.5 hours, EVOH-1 pellets containing sodium acetate, acetic acid, phosphoric acid and boric acid were obtained. Physical properties are shown in Table 3.

Example 16

The reaction was carried out in the same manner as in Example 15 to obtain ethylene-vinyl alcohol copolymer (EVOH-2) pellets, except that the total amount of the vinyl acetate was changed to VAM-2. Physical properties are shown in Table 3.

Example 17

The reaction was carried out in the same manner as in Example 15 to obtain ethylene-vinyl alcohol copolymer (EVOH-3) pellets, except that the total amount of the vinyl acetate was changed to VAM-3. Physical properties are shown in Table 3.

Example 18

The reaction was carried out in the same manner as in Example 15 to obtain ethylene-vinyl alcohol copolymer (EVOH-4) pellets, except that half of the vinyl acetate was changed to VAM-1 and the other half was changed to VAM-C1. Physical properties are shown in Table 3.

Example 19

The reaction was carried out in the same manner as in Example 15 to obtain ethylene-vinyl alcohol copolymer (EVOH-5) pellets, except that the total amount of the ethylene was changed to the ethylene derived from the petroleum. Physical properties are shown in Table 3.

Example 20

The reaction was carried out in the same manner as in Example 15 to obtain ethylene-vinyl alcohol copolymer (EVOH-6) pellets, except that half of the ethylene was changed to the ethylene derived from the petroleum. Physical properties are shown in Table 3.

Example 21

The reaction was carried out in the same manner as in Example 15 to obtain ethylene-vinyl alcohol copolymer (EVOH-7) pellets, except that the total amount of the ethylene was changed to the ethylene derived from the rice straw and the total amount of the vinyl acetate was changed to VAM-4. Physical properties are shown in Table 3.

Example 22

The reaction was carried out in the same manner as in Example 15 to obtain ethylene-vinyl alcohol copolymer (EVOH-8) pellets, except that the total amount of the ethylene was changed to the ethylene derived from the rice straw and the total amount of vinyl acetate was changed to VAM-5. Physical properties are shown in Table 3.

Example 23

The reaction was carried out in the same manner as in Example 15 to obtain ethylene-vinyl alcohol copolymer (EVOH-9) pellets, except that the total amount of the ethylene was changed to the ethylene derived from the rice straw and the total amount of vinyl acetate was changed to VAM-6. Physical properties are shown in Table 3.

Example 24

The reaction was carried out in the same manner as in Example 15 to obtain ethylene-vinyl alcohol copolymer (EVOH-10) pellets, except that the total amount of the ethylene was changed to the ethylene derived from the rice straw, half of the vinyl acetate was changed to VAM-4, and the other half of the vinyl acetate was changed to VAM-C1. Physical properties are shown in Table 3.

Example 25

The reaction was carried out in the same manner as in Example 15 to obtain ethylene-vinyl alcohol copolymer (EVOH-11) pellets, except that the total amount of the ethylene was changed to the ethylene derived from the petroleum and the total amount of the vinyl acetate was changed to VAM-4. Physical properties are shown in Table 3.

Example 26

The reaction was carried out in the same manner as in Example 15 to obtain ethylene-vinyl alcohol copolymer (EVOH-12) pellets, except that half of the ethylene was changed to the ethylene derived from the rice straw, the other half of the ethylene was changed to the ethylene derived from the petroleum, and the total amount of vinyl acetate was changed to VAM-4. Physical properties are shown in Table 3.

Comparative Example 3

The reaction was carried out in the same manner as in Example 8 to obtain ethylene-vinyl alcohol copolymer (EVOH-C1) pellets, except that the total amount of the vinyl acetate was changed to VAM-C1 and the total amount of the ethylene was changed to the ethylene derived from the petroleum. Physical properties are shown in Table 3.

TABLE 3

| | Raw material | | EVOH pellet | | | |
|---|---|---|---|---|---|---|
| | Ethylene | Vinyl acetate | Content of ethylene unit mol % | Degree of saponification mol % | Content of carboxylic acid ppm | Content of metal ion ppm |
| Example 15 | 100% derived from sugarcane (C4 plant) | VAM-1 | 32 | >99 | 250 | 200 |

TABLE 3-continued

| | | | | | | |
|---|---|---|---|---|---|---|
| Example 16 | 100% derived from sugarcane (C4 plant) | VAM-2 | 32 | >99 | 250 | 200 |
| Example 17 | 100% derived from sugarcane (C4 plant) | VAM-3 | 32 | >99 | 250 | 200 |
| Example 18 | 100% derived from sugarcane (C4 plant) | VAM-1/ VAM-C1 = 50/50 | 32 | >99 | 250 | 200 |
| Example 19 | 100% derived from petroleum | VAM-1 | 32 | >99 | 250 | 200 |
| Example 20 | 50% derived from sugarcane (C4 plant)/50% derived from petroleum | VAM-1 | 32 | >99 | 250 | 200 |
| Example 21 | 100% derived from rice straw (C3 plant) | VAM-4 | 32 | >99 | 250 | 200 |
| Example 22 | 100% derived from rice straw (C3 plant) | VAM-5 | 32 | >99 | 250 | 200 |
| Example 23 | 100% derived from rice straw (C3 plant) | VAM-6 | 32 | >99 | 250 | 200 |
| Example 24 | 100% derived from rice straw (C3 plant) | VAM-4/ VAM-C1 = 50/50 | 38 | >99 | 250 | 200 |
| Example 25 | 100% derived from petroleum | VAM-4 | 38 | >99 | 250 | 200 |
| Example 26 | 50% derived from rice straw (C3 plant)/50% derived from petroleum | VAM-4 | 32 | >99 | 250 | 200 |
| Comparative Example 3 | 100% derived from petroleum | VAM-C1 | 32 | >99 | 250 | 200 |

| | EVOH pellet | | | | |
|---|---|---|---|---|---|
| | Content of phosphorus compound ppm | Content of boron compound ppm | $^{14}C/C$ — | $\delta^{13}C$ ‰ | Evaluation Oxygen permeability mL/($m^2$ · day · atm) |
| Example 15 | 10 | 700 | $9.5 \times 10^{-13}$ | −12 | 0.3 |
| Example 16 | 10 | 700 | $9.5 \times 10^{-13}$ | −13 | 0.3 |
| Example 17 | 10 | 700 | $6.6 \times 10^{-13}$ | −17 | 0.3 |
| Example 18 | 10 | 700 | $6.6 \times 10^{-13}$ | −16 | 0.3 |
| Example 19 | 10 | 700 | $6.8 \times 10^{-13}$ | −16 | 0.3 |
| Example 20 | 10 | 700 | $8.4 \times 10^{-13}$ | −14 | 0.3 |
| Example 21 | 10 | 700 | $9.5 \times 10^{-13}$ | −38 | 0.3 |
| Example 22 | 10 | 700 | $9.5 \times 10^{-13}$ | −39 | 0.3 |
| Example 23 | 10 | 700 | $6.6 \times 10^{-13}$ | −34 | 0.3 |
| Example 24 | 10 | 700 | $6.6 \times 10^{-13}$ | −33 | 0.3 |
| Example 25 | 10 | 700 | $6.8 \times 10^{-13}$ | −41 | 0.3 |
| Example 26 | 10 | 700 | $8.4 \times 10^{-13}$ | −36 | 0.3 |
| Comparative Example 3 | 10 | 700 | $<1.0 \times 10^{-14}$ | −25 | 0.3 |

When $^{14}C/C$ and $\delta^{13}C$ values of EVOH-1 to EVOH-6 and EVOH-C1 obtained above were measured by the above method, the measured values show approximately the same as $^{14}C/C$ and $\delta^{13}C$ values of the vinyl acetate and the ethylene used. Further, $^{14}C/C$ and $\delta^{13}C$ of EVOH-1 to EVOH-6 are different from EVOH-C1 which is polymerized from the entirely vinyl acetate derived from the petroleum, and in EVOH-1 to EVOH-6, it is possible to identify the raw material by measuring $^{14}C/C$ and $\delta^{13}C$ of the ethylene-vinyl alcohol copolymer. Therefore, it is possible to trace the ethylene-vinyl acetate alcohol copolymer.

As shown in Table 3, each of the EVOH compositions of Examples 15 to 26, while partially using plant-derived raw materials, has high oxygen barrier property that are comparable to those derived from only fossil resources (the EVOH composition of Comparative Example 3).

Example 27

The reaction was carried out in the same manner as in Example 15 to obtain ethylene-vinyl alcohol copolymer (EVOH-13) pellets, except that 500 ppm of the methyl acetate was added to the vinyl acetate. As a result of comparing the physical properties of EVOH-1 and EVOH-13, EVOH-13 was found to be more improved in terms of film formation defects and roll end coloration. At this time, no difference was observed between EVOH-1 and EVOH-13 in $^{14}C/C$, $\delta^{13}C$ and oxygen permeability.

Example 28

The reaction was carried out in the same manner as in Example 15 to obtain ethylene-vinyl alcohol copolymer (EVOH-14) pellets, except that 350 ppm of the ethyl acetate was added to the vinyl acetate and the polymerization solvent was changed from methanol to ethanol. As a result of comparing the physical properties of EVOH-1 and EVOH-14, EVOH-14 was found to be more improved in terms of film formation defects and roll end coloration. At this time, no difference was observed between EVOH-1 and EVOH-14 in $^{14}C/C$, $\delta^{13}C$ and oxygen permeability.

Example 29

The reaction was carried out in the same manner as in Example 15 to obtain ethylene-vinyl alcohol copolymer (EVOH-15) pellets, except that 500 ppm of the methyl acetate was added to the vinyl acetate. As a result of comparing the physical properties of EVOH-1 and EVOH-15, EVOH-15 was found to be more improved in terms of film formation defects and roll end coloration. At this time, no difference was observed between EVOH-1 and EVOH-15 in $^{14}C/C$, $\delta^{13}C$ and oxygen permeability.

Example 30

The reaction was carried out in the same manner as in Example 21 to obtain ethylene-vinyl alcohol copolymer (EVOH-16) pellets, except that 350 ppm of the ethyl acetate was added to the vinyl acetate and the polymerization solvent was changed from methanol to ethanol. As a result of comparing the physical properties of EVOH-7 and EVOH-16, EVOH-16 was found to be more improved in terms of film formation defects and roll end coloration. At this time, no difference was observed between EVOH-7 and EVOH-16 in $^{14}C/C$, $\delta^{13}C$ and oxygen permeability.

Example 31

The reaction was carried out in the same manner as in Example 15 to obtain ethylene-vinyl alcohol copolymer (EVOH-17) pellets, except that 50 ppm of L-ascorbic acid was added to the vinyl acetate. As a result of comparing the physical properties of EVOH-1 and EVOH-17, EVOH-17 was found to be more improved in terms of film formation defects and roll end coloration. At this time, no difference was observed between EVOH-1 and EVOH-17 in $^{14}C/C$, $\delta^{13}C$ and oxygen permeability.

Example 32

The reaction was carried out in the same manner as in Example 15 to obtain ethylene-vinyl alcohol copolymer (EVOH-18) pellets, except that 50 ppm of erythorbic acid was added to the vinyl acetate. As a result of comparing the physical properties of EVOH-1 and EVOH-18, EVOH-18 was found to be more improved in terms of film formation defects and roll end coloration. At this time, no difference was observed between EVOH-1 and EVOH-18 in $^{14}C/C$, $\delta^{13}C$ and oxygen permeability.

Example 33

The reaction was carried out in the same manner as in Example 15 to obtain ethylene-vinyl alcohol copolymer (EVOH-19) pellets, except that 50 ppm of glucono delta lactone was added to the vinyl acetate. As a result of comparing the physical properties of EVOH-1 and EVOH-19, EVOH-19 was found to be more improved in terms of film formation defects and roll end coloration. At this time, no difference was observed between EVOH-1 and EVOH-19 in $^{14}C/C$, $\delta^{13}C$ and oxygen permeability.

Example 34

The reaction was carried out in the same manner as in Example 21 to obtain ethylene-vinyl alcohol copolymer (EVOH-20) pellets, except that 50 ppm of L-ascorbic acid was added to the vinyl acetate. As a result of comparing the physical properties of EVOH-7 and EVOH-20, EVOH-20 was found to be more improved in terms of film formation defects and roll end coloration. At this time, no difference was observed between EVOH-7 and EVOH-20 in $^{14}C/C$, $\delta^{13}C$ and oxygen permeability.

Example 35

The reaction was carried out in the same manner as in Example 21 to obtain ethylene-vinyl alcohol copolymer (EVOH-21) pellets, except that 50 ppm of erythorbic acid was added to the vinyl acetate. As a result of comparing the physical properties of EVOH-7 and EVOH-21, EVOH-21 was found to be more improved in terms of film formation defects and roll end coloration. At this time, no difference was observed between EVOH-7 and EVOH-21 in $^{14}C/C$, $\delta^{13}C$ and oxygen permeability.

Example 36

The reaction was carried out in the same manner as in Example 21 to obtain ethylene-vinyl alcohol copolymer (EVOH-22) pellets, except that 50 ppm of glucono delta lactone was added to the vinyl acetate. As a result of comparing the physical properties of EVOH-7 and EVOH-22, EVOH-22 was found to be more improved in terms of film formation defects and roll end coloration. At this time, no difference was observed between EVOH-7 and EVOH-22 in $^{14}C/C$, $\delta^{13}C$ and oxygen permeability.

From Examples 15, 21 and 31-36, when the vinyl acetate of the present invention is used and the vinyl acetate is polymerized alone or with other monomers in the coexistence of the polyvalent carboxylic acid, the hydroxycarboxylic acid, the hydroxylactone-based compound and the polymerization initiator, especially the vinyl acetate and the ethylene are copolymerized, the resulting ethylene-vinyl acetate copolymer is useful as a raw material for saponified ethylene-vinyl acetate copolymer, and the saponified ethylene-vinyl acetate copolymer obtained by saponifying such a copolymer can suppress fisheyes during film formation and is excellent in hue.

Example 37

The reaction was carried out in the same manner as in Example 7 to obtain a vinyl alcohol polymer (PVOH-9), except that 0.5 parts by mass of acetaldehyde dimethylacetal was added to the vinyl acetate. As a result of visually confirming PVOH-1 and PVOH-9, PVOH-9 was whiter and had better hue. At this time, no difference was observed between PVOH-1 and PVOH-9 in $^{14}C/C$ and $\delta^{13}C$.

Example 38

The reaction was carried out in the same manner as in Example 7 to obtain a vinyl alcohol polymer (PVOH-10), except that 4 parts by mass of the acetaldehyde dimethylacetal was added to the vinyl acetate. As a result of visually confirming PVOH-1 and PVOH-10, PVOH-10 was whiter and had better hue. At this time, no difference was observed between PVOH-1 and PVOH-10 in $^{14}C/C$ and $\delta^{13}C$.

Example 39

The reaction was carried out in the same manner as in Example 7 to obtain a vinyl alcohol polymer (PVOH-11), except that 4 parts by mass of the acetaldehyde dimethylacetal and 5 ppm of citric acid were added to the vinyl acetate. As a result of visually confirming PVOH-1 and PVOH-11, PVOH-11 was whiter and had better hue. At this time, no difference was observed between PVOH-1 and PVOH-11 in $^{14}C/C$ and $\delta^{13}C$.

Example 40

The reaction was carried out in the same manner as in Example 7 to obtain a vinyl alcohol polymer (PVOH-12), except that 4 parts by mass of the acetaldehyde dimethylacetal and 10 ppm of citric acid were added to the vinyl acetate. As a result of visually confirming PVOH-1 and PVOH-12, PVOH-12 was whiter and had better hue. At this time, no difference was observed between PVOH-1 and PVOH-12 in $^{14}C/C$ and $\delta^{13}C$.

Example 41

The reaction was carried out in the same manner as in Example 11 to obtain a vinyl alcohol polymer (PVOH-13), except that 0.5 parts by mass of the acetaldehyde dimethylacetal was added to the vinyl acetate. As a result of visually confirming PVOH-5 and PVOH-13, PVOH-13 was whiter and had better hue. At this time, no difference was observed between PVOH-5 and PVOH-13 in $^{14}C/C$ and $\delta^{13}C$.

Example 42

The reaction was carried out in the same manner as in Example 11 to obtain a vinyl alcohol polymer (PVOH-14), except that 4 parts by mass of the acetaldehyde dimethylacetal was added to the vinyl acetate. As a result of visually confirming PVOH-5 and PVOH-14, PVOH-14 was whiter and had better hue. At this time, no difference was observed between PVOH-5 and PVOH-14 in $^{14}C/C$ and $\delta^{13}C$.

Example 43

The reaction was carried out in the same manner as in Example 11 to obtain a vinyl alcohol polymer (PVOH-15), except that 4 parts by mass of the acetaldehyde dimethylacetal and 5 ppm of the citric acid were added to the vinyl acetate. As a result of visually confirming PVOH-5 and PVOH-15, PVOH-13 was whiter and had better hue. At this time, no difference was observed between PVOH-5 and PVOH-15 in $^{14}C/C$ and $\delta^{13}C$.

Example 44

The reaction was carried out in the same manner as in Example 11 to obtain a vinyl alcohol polymer (EVOH-16), except that 4 parts by mass of the acetaldehyde dimethylacetal and 10 ppm of the citric acid were added to the vinyl acetate. As a result of visually confirming PVOH-5 and PVOH-16, PVOH-16 was whiter and had better hue. At this time, no difference was observed between PVOH-5 and PVOH-15 in $^{14}C/C$ and $\delta^{13}C$.

From Examples 7, 14 and 37 to 44, by using the vinyl acetate to which the acetaldehyde dimethylacetal was added, the vinyl acetate polymer with good quality could be obtained, and such a polymer is also useful as a raw material for obtaining a vinyl alcohol polymer with excellent hue.

Example 45

A continuous polymerization tank equipped with a reflux condenser, a raw material supply line, a reaction solution take-out line, a thermometer, a nitrogen inlet, an ethylene inlet and a stirring blade was used. 671 L/hr of VAM-1, 148 L/hr of methanol, and 1.0 L/hr of 1% methanol solution of n-propylperoxydicarbonate as an initiator were continuously supplied to the continuous polymerization tank using metering pumps. Ane amount of the n-propyl peroxydicarbonate added was 0.00132% by mass with respect to VAM-1. The ethylene pressure in the continuous polymerization tank was adjusted to 0.23 MPa. Ethylene derived from sugarcane (manufactured by Braskem SA) was used as the ethylene. The polymerization liquid was continuously taken out from the continuous polymerization tank so that a liquid level in the continuous polymerization tank was kept constant. The rate of polymerization at the outlet of the continuous polymerization tank was adjusted to 26%. At this time, propanethiol was continuously added as a chain transfer agent so that a concentration of the propanethiol in the system (concentration relative to the residual vinyl acetate in the polymerization solution continuously extracted as 100) was 0.00042% by mass with respect to VAM-1. A residence time in the continuous polymerization tank was 5 hours. The temperature at the outlet of the continuous polymerization tank was set at 60 °C. The polymerization liquid is recovered from the continuous polymerization tank, and methanol vapor is introduced into the polymerization liquid while heating to 75 °C in a hot water bath to remove residual vinyl acetate so that a methanol solution (EVAc concentration: 32%) of an ethylene-modified vinyl ester polymer (hereinafter, may be referred to as "EVAc") was obtained. The average residence time in the removal step was 2 hours, and the amount of vinyl acetate remaining in the obtained methanol solution of the ethylene-modified vinyl ester polymer was 0.1%.

Subsequently, the saponification reaction is carried out at 40 °C for 1 hour at a water content of 0.5% and using sodium hydroxide as a saponification catalyst at a molar ratio of 0.012 to the ethylene-modified vinyl ester polymer. The obtained polymer was immersed in methanol and washed. Then the solvent is removed by centrifugation and then dried to obtain a composition containing an ethylene-vinyl alcohol copolymer (EVOH-23) as a main component with the content of the ethylene unit of 2 mol%, the viscosity-average degree of polymerization of 1,700, the degree of saponification of 98.5 mol%, the content of the 1,2-glycol bond of 1.6 mol% and the content of the propyl group of 0.0061 mol% at one terminal end and containing 0.42% by mass of sodium acetate.

Using the resulting composition, the solubility of EVOH-23 when heated at 90 °C for 5 hours, the viscosity stability of the aqueous solution and the hue were measured. As a result, the solubility, the viscosity stability of aqueous solution, and the hue (YI) were good.

Example 46

Figure 2:
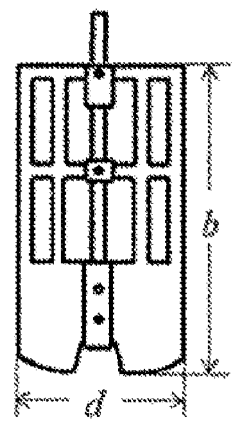
FIG. 2 is a schematic diagram of a stirring blade used in Example 46.

A schematic diagram of the polymerization apparatus used is shown in FIG. 1, and a schematic diagram of the stirring blade is shown in FIG. 2. Ethylene was introduced into a substantially cylindrical polymerization tank 1 equipped with a Maxblend blade [manufactured by Kobelco Eco-Solutions Co., Ltd., stirring blade diameter (diameter) d: 1.1 m, blade (paddle) width b: 1.5 m] as a stirring blade 8 [capacity: 7,000 L, tank inner diameter D: 1.8 m] from a conduit 5 so that the ethylene pressure in the tank was 0.23 MPa, and 1% by mass of methanol solution of 2,2'-azobis-(4-methoxy-2,4-2,4-(4-methoxy-2,4-dimethylvaleronitrile) as a polymerization initiator was introduced into the polymerization tank 1 from a conduit 6 at a rate of 3 L/hr. Ethylene derived from sugarcane (manufactured by Braskem SA) was used as the ethylene. Further, a VAM-1-containing liquid (VAM-1: 777 L/hr, methanol: 170 L/hr) was introduced into the polymerization tank 1 via an introduction pipe 10 and a heat exchanger 2. Further, an ethylene-containing gas was introduced from the polymerization tank 1 through a conduit 3 into the heat exchanger 2. The VAM-1-containing liquid flowed down along the surface of the tube to absorb ethylene, was poured into the polymerization tank 1 via a conduit 4, mixed with the reaction liquid and subjected to continuous polymerization with ethylene. A polymerization liquid was continuously taken out from a conduit 9 so that the liquid level in the polymerization tank 1 was kept constant. The rate of polymerization of VAM-1 at the outlet of polymerization tank 1 was adjusted to 30%. A stirring power Pv per unit volume was 2.2 kW/m3, and the Froude number Fr was adjusted to 0.13. The reaction solution was stirred while the entire blade (paddle) was immersed in the reaction solution and the liquid surface was close to the upper end of the blade (paddle). A residence time of the reaction solution in the polymerization tank was 5 hours. The temperature at the outlet of the polymerization tank was 60 °C. Unreacted vinyl acetate monomer was removed by introducing methanol vapor into the polymer solution that was continuously taken out to obtain a methanol solution of ethylene-vinyl acetate copolymer (concentration: 32% by mass).

Subsequently, a methanol solution of sodium hydroxide (concentration: 4% by mass) was added to the methanol solution (concentration: 32% by mass) of the ethylene-vinyl acetate copolymer obtained in the polymerization step so that a molar ratio of the sodium hydroxide to vinyl acetate units in the ethylene-vinyl acetate copolymer is 0.012. Further, 0.00018 parts by mass of a methanol solution of sorbic acid (concentration 10% by mass) is added to 100 parts by mass of the ethylene-vinyl acetate copolymer, and the obtained mixture was mixed with a static mixer, placed on a belt, and held at 40 °C for 18 minutes to allow the saponification reaction to proceed. Thereafter, the mixture was pulverized and dried to obtain an ethylene-vinyl alcohol copolymer (EVOH-24). As a result of analysis of EVOH-24, the content of ethylene units was 2 mol%, the viscosity-average degree of polymerization was 1,700, the degree of saponification was 98.5 mol%, the content of the structure (I) was 0.00114 mol%, and the content of the structure (II) was 0.0002 mol% and the block character of the ethylene unit was 0.95.

Example 47

83.0 kg of VAM-1 and 26.6 kg of methanol were charged into a 250 L pressurized reactor equipped with a jacket, a stirrer, a nitrogen inlet, an ethylene inlet, and an initiator addition port, heated to 60 °C, and then nitrogen bubbling was performed for 30 minutes to replace an inside of the reactor with nitrogen. Then, ethylene was introduced under pressure so that the reactor pressure (ethylene pressure) was 3.6 MPa. The ethylene derived from sugarcane (manufactured by Braskem SA) was used. After adjusting the temperature in the reactor to 60 °C, a 2.5 g/L methanol solution of 2,2'-azobis(2,4-dimethylvaleronitrile) as an initiator was initially supplied in an amount of 362 mL and continuously supplied in an amount of 1,120 mL/hr. The ethylene pressure was maintained at 3.6 MPa and the polymerization temperature at 60 °C during the polymerization. When the polymerization rate of the vinyl acetate reached 40%, sorbic acid was added to the reactor and the mixture was cooled to terminate the polymerization. After the reactor was opened to remove ethylene, nitrogen gas was bubbled through to completely remove ethylene. After removing unreacted vinyl acetate under reduced pressure, methanol was added to the obtained ethylene-vinyl acetate copolymer to obtain a 20% by mass methanol solution.

The obtained methanol solution of the ethylene-vinyl acetate copolymer is charged into a saponification reactor, and 2 mol/L methanol solution of sodium hydroxide is added to the saponification reactor so as to have 3 equivalents with respect to the vinyl ester component in the copolymer. Then, methanol was added to adjust a concentration of the copolymer to 5%. This solution was heated to 60 °C and saponified for 3 hours while stirring. At this time, for the last 1 hour, an ultrasonic cleaner "US CLEANER USK-2R" was used to react while irradiating ultrasonic waves through the reactor at an output of 80 W and a frequency of 40 kHz. After that, acetic acid and water were added to stop the saponification reaction and precipitate an ethylene-vinyl alcohol copolymer. The precipitated ethylene-vinyl alcohol copolymer was recovered and finely ground to obtain hydrous chips, washed with an acetic acid aqueous solution and ion-exchanged water, and further immersed in an aqueous solution containing sodium acetate and acetic acid. After separating and deliquoring the aqueous solution and the hydrous chips, the hydrous chips was placed in a hot air dryer and dried at 80 °C for 3 hours and then at 110 °C for 35 hours to obtain an ethylene-vinyl alcohol copolymer (EVOH-25) as dry chips. As a result of analysis of EVOH-25, the degree of saponification was 99.9 mol% or more, the content of the structure (I) was 0.0071 mol%, and the content of the structure (II) was 0.0027 mol%. Further, the contents of the sodium and the acetic acid were 180 ppm and 300 ppm, respectively.

Example 48

Tracing will be done by the following method.

A barrier layer containing ethylene-vinyl alcohol copolymer from 10 samples of commercially available packaging containers is taken out.

For this sample, $^{14}C/C$ and $\delta^{13}C$ are obtained by the above method. By comparing the obtained values with the values of $^{14}C/C$ and $\delta^{13}C$ recorded in advance at the time of manufacture, it is determined whether or not the product is an in-house product.

Example 49

Films 1 to 6 were obtained by the method described above using EVOH-1 to EVOH-6 obtained in Examples 8 to 13. The obtained films 1 to 6 were recovered as packaging bags 1 to 6, respectively. $^{14}C/C$ and $\delta^{13}C$ values of the recovered material, determined by the method described above, were consistent with those obtained in Examples 8-13.

INDUSTRIAL APPLICABILITY

The vinyl acetate of the present invention differs from the conventional vinyl acetate in the value of $^{14}C/C$. Accordingly, a vinyl acetate polymer containing vinyl acetate as a monomer unit obtained by polymerizing the vinyl acetate of the present invention and the vinyl alcohol polymer which is the saponified product thereof also have a value of $^{14}C/C$ different from that of the conventional product. Using this difference, it is possible to determine whether the vinyl acetate polymer or the vinyl alcohol polymer recovered from the market is the one using the vinyl acetate of the present invention, and it is possible to trace in-house products.

EXPLANATION OF REFERENCE NUMERAL

1: Polymerization tank
2: Heat exchanger
3 to 7: Conduit
8: stirring blade
9: Reaction liquid conduit
10: vinyl ester introduction pipe
11, 12: refrigerant pipe
13: Gas exhaust pipe
21: Maxblend blade

What is claimed is:

1. A vinyl acetate having a ratio of carbon-14 to total carbon of $1.0\times10^{-14}$ or more and less than $1.2\times10^{-12}$.

2. The vinyl acetate as claimed in claim 1, having a carbon stable isotope ratio of −20‰ or more.

3. The vinyl acetate as claimed in claim 1, having a carbon stable isotope ratio of less than −20‰.

4. The vinyl acetate as claimed in claim 1, further comprising a sulfur component in an amount of more than 0 ppm and 100 ppm or less.

5. The vinyl acetate as claimed in claim 4, wherein the sulfur component is dimethylsulfide or dimethylsulfoxide.

6. The vinyl acetate as claimed in claim 1, further comprising a saturated acetate ester in an amount of 10 ppm to 1,500 ppm.

7. The vinyl acetate as claimed in claim 6, wherein the saturated acetate ester is at least one of methyl acetate and ethyl acetate.

8. The vinyl acetate as claimed in claim 1, further comprising a polymerization inhibitor in an amount of more than 0 ppm and 100 ppm or less.

9. The vinyl acetate as claimed in claim 1, further comprising at least one compound selected from a polyvalent carboxylic acid, a hydroxycarboxylic acid and a hydroxylactone-based compound in an amount of 1 ppm to 500 ppm.

10. The vinyl acetate as claimed in claim 1, furhter comprising acetaldehyde dimethylacetal in an amount of 0.001 to 10 parts by mass.

11. A vinyl acetate polymer containing the vinyl acetate as claimed in claim 1 as a monomer unit.

12. A vinyl alcohol polymer obtained by saponifying the vinyl acetate polymer as claimed in claim 11.

13. The vinyl alcohol polymer as claimed in claim 12, further containing ethylene units in a content of 1 mol% or more and 60 mol% or less.

14. The vinyl alcohol polymer as claimed in claim 12, having a degree of saponification of 80 mol% or more.

15. The vinyl alcohol polymer as claimed in claim 12, having a viscosity-average polymerization degree of 200 or more and 5,000 or less.

16. The vinyl alcohol polymer as claimed in claim 12, wherein a content of 1, 2-glycol bond is in the range of 0.2 mol% or more and 2 mol% or less.

17. The vinyl alcohol polymer as claimed in claim 12, having a carbon stable isotope ratio of −20‰ or more.

18. The vinyl alcohol polymer as claimed in claim 12, having a carbon stable isotope ratio of less than −20‰.

19. The vinyl alcohol polymer as claimed in claim 12, containing a sulfur component in an amount of more than 0 ppm and 100 ppm or less.

20. The vinyl alcohol polymer as claimed in claim 19, wherein the sulfur component is dimethylsulfide or dimethylsulfoxide.

21. The vinyl alcohol polymer as claimed in claim 12, wherein a content of ethylene units is in the range of 1 mol% or more and 15 mol% or less, and a degree of saponification is in the range of 85 mol% or more and 99.9 mol% or less, and wherein the vinyl alcohol polymer has a propyl group at a terminal end thereof and a content of the propyl group with respect to total monomer units is in the range of 0.0005 mol% or more and 0.1 mol% or less.

22. The vinyl alcohol polymer as claimed in claim 12, wherein the vinyl alcohol polymer has an alkoxy group at a terminal end thereof and a content of the alkoxy group with respect to total monomer units is in the range of 0.0005 mol% or more and 1 mol% or less.

23. The vinyl alcohol polymer as claimed in claim 12, wherein the vinyl alcohol polymer has a following structure (I) and structure (II) at a terminal end thereof and a total content of the structure (I) and the structure (II) with respect to total monomer units constituting the vinyl alcohol polymer is in the range of 0.001 mol% or more and 0.1 mol% or less;

[Formula 1]

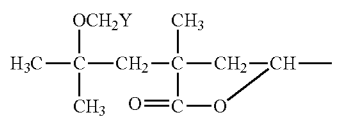

(I)

where Y is a hydrogen atom or a methyl group;

[Formula 2]

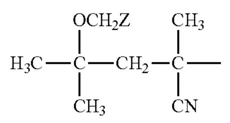

(II)

where Z is a hydrogen atom or a methyl group.

24. The vinyl alcohol polymer as claimed in claim 23, wherein a content of ethylene units is in the range of 1 mol% or more and 15 mol% or less, and a degree of saponification is in the range of 85 mol% or more and 99.9 mol% or less, and wherein a molar ratio R [I/(I+II)] of the structure (I) to a total of the structure (I) and the structure (II) satisfies a following formula (1):

$$R<0.92-Et/100 \quad (1)$$

where Et is the content of the ethylene units (mol%).

25. The vinyl alcohol polymer as claimed in claim 13, wherein a block character of ethylene units is in the range of 0.90 to 0.99.

26. The vinyl alcohol polymer as claimed in claim 23, wherein a content of ethylene units is in the range of 15 mol% or more and 60 mol% or less, and a degree of saponification is in the range of 85 mol% or more and 99.9 mol% or less, and wherein a total content of the structure (I) and the structure (II) with respect to total monomer units constituting the vinyl alcohol polymer is in the range of 0.002 mol% or more and 0.02 mol% or less, and a molar ratio R [I/(I+II)] of the structure (I) to a total of the structure (I) and the structure (II) satisfies a following formula (2) expressed using the content of the ethylene units Et in the vinyl alcohol polymer;

$$0.8<R+Et/100 \quad (2).$$

27. A method for tracing a polymer comprising using the vinyl acetate of claim 1.

28. The method of claim 27, wherein a carbon stable isotope ratio of the vinyl acetate is −20‰ or more.

29. The method of claim 27, wherein a carbon stable isotope ratio of the vinyl acetate is less than −20‰.

30. A method for tracing a polymer comprising using a vinyl acetate polymer containing the vinyl acetate as claimed in claim 1 as a monomer unit.

31. A method for tracing a polymer comprising using a vinyl alcohol polymer obtained by saponifying the vinyl acetate polymer as claimed in claim 11.

* * * * *